US006482646B1

(12) United States Patent
Gindullis et al.

(10) Patent No.: US 6,482,646 B1
(45) Date of Patent: Nov. 19, 2002

(54) PLANT PROTEINS THAT INTERACT WITH NUCLEAR MATRIX PROTEINS AND FUNCTION AS TRANSCRIPTIONAL ACTIVATORS

(75) Inventors: Frank Gindullis, Greenville, DE (US); Iris Meier, Greenville, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/187,999

(22) Filed: Nov. 6, 1998

(51) Int. Cl.[7] .......................... C12N 15/29; C12N 5/10; C12N 15/70; C12N 15/82
(52) U.S. Cl. ................. 435/419; 435/69.1; 435/252.33; 435/468; 536/23.6
(58) Field of Search ................................ 435/69.1, 471, 435/410, 419, 4, 468, 252.33; 536/23.1, 23.53, 23.6; 800/278, 283, 290

(56) References Cited

U.S. PATENT DOCUMENTS

| | | |
|---|---|---|
| 5,652,340 A | 7/1997 | Kahwi-Shigematsu et al. |
| 5,773,689 A | 6/1998 | Thompson et al. |

FOREIGN PATENT DOCUMENTS

| | | |
|---|---|---|
| CA | 2 150 039 A | 8/1996 |
| WO | WO97 30164 A | 8/1997 |
| WO | WO 97 35983 A | 10/1997 |

OTHER PUBLICATIONS

McKeon et al., *Nature,* 319, 463–468, 1986.
Schafer et al., *Annu. Rev. Genet.,* 30, 209–237, 1992.
Furukawa et al., *EMBO J.,* 14, 1626–1636, 1995.
Berezney et al., *Biochem. Biophys. Res. Comm.,* 60, 1410–1417, 1974.
Mirkowitch et al., *Cell,* 39, 223–232, 1984.
Gasser et al., *Trends Genet.,* 3, 16–22, 1987.
Phi–Wan et al., *EMBO J.,* 7, 655–664, 1988.
von Kries et al., *Cell,* 64, 123–135, 1991.
Dickinson et al., *Cell,* 70, 631–645, 1992.
Romig et al., *EMBO J.,* 11, 3431–3440, 1992.
Tsutsui et al., *J. Biol. Chem.,* 268, 12886–12894, 1993.
Renz et al., *Nucleic Acids Res.,* 24, 843–849, 1996.
Luderus et al., *Mol. Cell. Biol.,* 14, 6297–6305, 1994.
Beven et al., *J. Cell Sci,* (1991) 98 (3), 293–302.
McNulty et al., *J. Cell Sci.,* 103, 407–414, 1992.
Hall et al., *Proc. Natl. Acad. Sci. USA,* 88, 9320–9324, 1991.
Breyne et al., *Plant Cell,* 4, 463–471, 1992.
Allen et al., *Plant Cell,* 5, 603–613, 1993.
Allen et al., *Plant Cell,* 8, 899–913, 1996.
van der Geest et al., *Plant J.,* 6, 413–423, 1994.
Mlynarova et al., *Plant Cell,* 6, 417–426, 1994.
Meier et al., *Plant Cell,* 8, 2105–2115, 1996.

Newman, T. et al., 28658 Lambda–PRL2 *Arabidopsis thaliana* cDNA clone 42A7XP 3', mRNA sequence, XP002139209, Sep. 13, 1997.
Nakamura, Y., et al., *Arabidopsis thaliana* genomic DNA, chromosome 5, P1 clone: MMG4, Jan. 28, 1998, XP002139210.
Sasaki, T., *Oryza sativa* mRNA for chitinase, complete cds., Dec. 11, 1997, XP002139211.
Wing, R. A. et al., nbxb0031H06r CUGI Rice BAC Library *Oryza sativa* genomic clone nbxb0031H06r, genomic survey sequence., Nov. 4, 1998, XP002139212.
Nazar, R. N., et al., Human ribosomal DNA complete repeating unit, Dec. 16, 1994, XP002139213.
Rounslley, S. D., et al., T25C12TFD TAMU *Arabidopsis thaliana* genomic clone T25C12, genomic survey sequence, Sep. 25, 1998, XP002139214.
Paek, N. C. et al., *B.oleracea* mRNA for asparagine synthetase, Feb. 13, 1995, XP002139215.
Rounsley, S. D. et al., T25F10TFB TAMU *Arabidopsis thaliana* genomic clone T25F10, genomic survey sequence, Apr. 3, 1998, XP002139216.
Quesada, A., et al., *N. plumbaginifolia* nRNA for nitrate transporter Nrt2;1Np, Jun. 19, 1997, XP002139217.
Wing, R. A. et al., nbxb0019C20r CUGI Rice BAC Library *Oryza sativa* genomic clone nbxb0019C20r, genomic survey sequence., Oct. 23, 1998, XP002139218.
Uchimiya, H., Rice cDNA SS285, May 5, 1998, XP002139219.
Grimes, H. D. et al., Glycine max sucrose binding protein (sbp) mRNA, complete cds, Jan. 28, 1993, XP002139220.
Gindullis, Frank et al., MAF1, a novel plant protein interacting with matrix attachment region binding protein MFP1, is located at the nuclear envelope, Plant Cell, Sep. 1999 p. 1755–1767, XP002139221.
Alcala, J, et al., EST263924 tomato callus, TAMU *Lycopersicon esculetum* cDNA clone cLEC4G18, mRNA sequence, Jul. 28, 1999, XP002139222.
Sasaki, T., *Oryza sativa* cDNA, partial sequence (C53122_7A), Jun. 7, 1999, XP002139223.
Shoemaker, R. et al., sb83c12.yl Gm–c1010 Glycine max cDNA clone Genome Systems Clone ID: Gm–c1010–1583 5', mRNA sequence, Aug. 4, 1999, XP002139224.

(List continued on next page.)

*Primary Examiner*—David T. Fox

(57) ABSTRACT

This invention pertains to nucleic acid molecules encoding plant proteins that interact with nuclear matrix proteins and function as transcriptional activators. Using MFP1 and the yeast two-hybrid screen, MAF1 and NMP1 were isolated and sequenced and determined to be novel. Using MAF1 for a second yeast two-hybrid screen, four additional novel proteins have been isolated, sequenced and identified as FLIP1, FLIP2, FLIP3 and FLIP4. The proteins of the instant invention can be used to enhance the level of gene expression in plants and other eukaryotic organisms.

8 Claims, 5 Drawing Sheets

OTHER PUBLICATIONS

Shoemaker, R. et al., se09g12.y1 Gm–c1013 Glycine max cDNA clone Genome Systems Clone ID: Gm–1013–3071 5', mRNA sequence. XP002139225.

Alcala, J. et al., EST243802 tomato ovary, TAMU *Lycopersicon esculentum* cDNA clone cLED488, mRNA sequence, Mar. 17, 1999, XP002139226.

D'Ascenzo, M., et al, EST255081 tomato resistant, Cornell *Lycopersicon esculentum* cDNA clone cLER9E15, mRNA sequence, Jun. 30, 1999, XP002139227.

Bobb, A. J. et al., PVALF, an embryo–specific acidic transcriptional activator enhancesgene expression from phaseolin and phytohemagglutinin promoters, Plant Journal, GB, Blackwell Scientific Publications, Oxford, vol. 8, No. 3, Jan. 1, 1995, XP002063683.

Guyer et al., Activation of latent transgenes in Arabidopsis using a hybrid transcription factor, Genetics, US, Genetices Society of America, Austin, TX, vol. 149, No. 2 Jun. 1998, pp. 633–639, XP002099061.

Estruch et al., Plant activating sequences: positively charged peptides are functional as transcriptional activation domains, Nucleic Acids Research, GB, Oxford University Press, Surrey, vol. 22, No. 19, Jan. 1, 1994, XP002083112.

Schwechheimer, C., et al., The activities of acidic and glutamine–rich transcriptional activation domains in plant cells: design of modular transcription factors for high–level expression, Plant Molecular Biology, Jan. 1998, XP002139229.

FIG. 1A

```
        K S R S A P A A A S E G E S K P S E L P A D A S E P S S A S G L T G E V S S V E   MAF1
110     K S R S A P A A A S E G E S K P S E L P A D A S E P S S A S G L T G E V S S V E   MAF1
115     K S R S A D A K A D P - - - - - - - - - - - - - - - - - - - - - - - - - - - - -   ctaln.pk0074.f12
116     K A R A P P S - - - - - - - - - P S A E A L A P D A P E A - - - - - - - - - - -   ssl.pk0021.e2
 68     K A R A A E I - - - - - - - - - - - - - - - - - - - - P A A V E G V A A A - - -   sel.pk0050.g5
 79     - - - - - - - - - - - - - - - - - - - - - - - - - - - - A A V E G V A A A V S -   wleln.pk0104.e10
119     K A R T E A A S S V S E S Y P G G G S L L P S - - - - P S A E E G V A A S V S -   ectlc.pk0001.11
 63     - - - - - - - - - - - - - - - - - - - - - - - - - - - - A L L S L P K F R - - -   pps.pk0009.b7

150     T E P - - - - - - - - - - - - - - - - - - - - - - - - - - - - - - - - - - - - -
139     - - - - - - - - - - - - - - - - - - - - - - - - - - - - - - - - - - - - - - - -
135     - - D - - - - - - - - - - - - - - - - - - - - - - - Q P A A
 87     - - D - - - - - - - - - - - - - - - - - - - - - - - - - - -
 79     - - - - - - - - - - - - - - - - - - - - - - - - - - - - - - -
159     A A S T L P M E E T W A S F X C L P
 63     - - G - - - - - - - - - - - - - - -
```

| | |
|---|---|
| MAF1 | Seq. ID No. 2 |
| ctaln.pk0074.f12 | Seq. ID No. 19 |
| ssl.pk0021.e2 | Seq. ID No. 21 |
| sel.pk0050.g5 | Seq. ID No. 23 |
| wleln.pk0104.e10 | Seq. ID No. 25 |
| ectlc.pk0001.11 | Seq. ID No. 27 |
| pps.pk0009.b7 | Seq. ID No. 29 |

```
321  I A R E R G E D I S L      NMP1            Seq. ID No.  4
320  V A R E Q G G T L          cbn2.pk0003.a12 Seq. ID No. 31
126                             wrl.pk0025.c2   Seq. ID No. 33
121                             plht.pk0024.h5  Seq. ID No. 35
 66                             bsh.pk0011.e4   Seq. ID No. 37
```

FIG. 2C

PLANT PROTEINS THAT INTERACT WITH NUCLEAR MATRIX PROTEINS AND FUNCTION AS TRANSCRIPTIONAL ACTIVATORS

FIELD OF THE INVENTION

This invention is in the field of plant molecular biology. More specifically, this invention pertains to nucleic acid fragments encoding proteins that interact with nuclear matrix proteins and function as transcriptional activators.

BACKGROUND OF THE INVENTION

The nuclear matrix hypothesis proposes a structural framework for the eukaryotic nucleus that is similar to the cytoskeleton. To date, its best characterized component is the lamina, a filamentous protein network that lines the inner membrane of the nuclear envelope. Major components of the lamina include a group of intermediate-filament (IF) proteins, collectively known as nuclear lamins, that are classified as type A, B, and C (McKeon et al., Nature 319:463–468 (1986)). Lamin B is attached to the inner nuclear membrane via a C-terminal C15 farnesyl group (Schafer et al., Annu. Rev. Genet. 30:209–237 (1992)), whereas lamins A and C bind to lamin B. Other integral membrane proteins interact with lamin B and most likely stabilize the membrane attachment of lamins (Furukawa et al., EMBO J. 14:1626–1636 (1995)). Recent studies have also demonstrated the ability of lamins A and B to bind DNA, suggesting a role for mammalian lamins in anchoring chromatin to the nuclear envelope. The interaction between nuclear envelope, lamina, and chromatin is considered to be of fundamental importance for higher order chromosome organization, as well as the assembly and disassembly of the nuclear envelope during mitosis (Furukawa et al., EMBO J. 14:1626–1636 (1995)).

The nuclear matrix is a second structural skeleton that has been biochemically defined as the insoluble component that remains after treatment of isolated nuclei with DNase I and extraction of proteins with high-salt solutions (Berezney et al., Biochem. Biophys. Res. Comm. 60:1410–1417 (1974)) or the chaotropic agent lithium diiodosalicylate (Mirkowitch et al., Cell 39:223–232 (1984)). Chromatin binds to the nuclear matrix via matrix attachment regions (MARs) in the DNA. MARs are generally AT-rich DNA sequences that are several hundred base pairs long and localized to noncoding regions of the DNA, but often flanking genes (Gasser et al., Trends Genet. 3:16–22 (1987)). However, there is no consensus sequence known for MARS. The significance of structural characteristics for MARs such as DNA bending and a narrow minor groove due to oligo(dA) tracts has been previously proposed. MARs have been shown to increase transcriptional activity of a linked gene and to confer position-independent, copy-number dependent expression in stably transfected cells (Phi-Wan et al., EMBO J. 7:655–664 (1988)).

A small number of MAR binding proteins have been identified from animal nuclei, and they are considered to be components of the nuclear matrix (von Kries et al., Cell 64:123–135 (1991); Dickinson et al., Cell 70:631–645 (1 992); Romig et al., EMBO J. 11:3431–3440 (1992); Tsutsui et al., J. Biol. Chem. 268:12886–12894 (1993); Renz et al., Nucleic Acids Res. 24:843–849 (1996); U.S. Pat. No. 5,652, 340). In addition, it has been shown that lamins specifically bind to MARs (Luderus et al., Mol. Cell. Biol. 14:6297–6305 (1994)). The specific interaction between DNA and the nuclear matrix/nuclear lamina is most likely an important mechanism for long-range gene regulation and higher order chromatin organization (Gasser et al., Trends Genet. 3:16–22 (1987)).

Most investigations into structural components of the nucleus have focused on proteins in vertebrates and Drosophila. Significantly less information is available for other eukaryotes, and in particular for plants. Proteins that are immunologically related to animal IF proteins and lamins have been detected in pea and carrot nuclei (Beven et al., J. Mol. Biol. 228:41–57 (1991); McNulty et al., J. Cell Sci. 103:407–414 (1992)). Plant nuclear matrix preparations that bind to animal MARs have been reported, suggesting that proteins with similar DNA binding specificities exist in plants as well (Hall et al., Proc. Natl. Acad. Sci. USA 88:9320–9324 (1991)).

Effects of MARs on gene expression in plants have been reported, but have been quite variable. In some experimental systems, no reduction of variability but an increase in expression level has been reported (Breyne et al., Plant Cell 4:463–471 (1992); Allen et al., Plant Cell 5:603–613 (1993); Allen et al., Plant Cell 8:899–913 (1996); U.S. Pat. No. 5,773,689). Other authors have found no significant increase in expression level, but a reduction of variability (van der Geest et al., Plant J. 6:413–423 (1994); Mlynarova et al., Plant Cell 6:417–426 (1994)). It is not clear what causes these observed differences, but they will most probably be due to the fact that MARs establish different molecular interactions, which might either depend on the features of the MAR itself or on the specific molecular environment of the transformed cell/tissue. The routine use of MARs for strategies to improve transgene expression will greatly depend on the characterization of the proteins involved in DNA-nuclear matrix attachment and the factors responsible for the observed increase in gene expression.

Currently, no sequence information is available for plant lamin-like proteins. However, the cloning of the cDNA for a plant MAR-binding protein, MFP1, from tomato has been reported (Meier et al., Plant Cell 8:2105–2115 (1996)). MFP1 has structural features of a filament-like protein and it preferentially binds to MAR DNA sequences from both plants and animals. In contrast to other known MAR binding proteins, MFP1 contains a hydrophobic N-terminal amino acid sequence that might function as a membrane-spanning domain. MFP1, therefore, has features of a novel anchor protein that most likely connects chromatin via MAR DNA with the nuclear envelope and nuclear filament proteins.

In order to routinely use the attachment of transgenes to the nuclear matrix improve gene expression, it will be necessary to further characterize the elements involved in this process and to better understand the underlying mechanisms. Thus, a need exists to identify and characterize additional nuclear matrix proteins. The present invention presents six previously unknown proteins that are localized in the nuclear matrix, bind to a MAR-binding protein or to a protein that binds to a MAR-binding protein, or are able to increase gene expression.

SUMMARY OF THE INVENTION

Applicants provide a method for regulating gene expression in a stably transformed transgenic plant cell which comprises combining into the genome of the plant cell:
(a) a first chimeric gene comprising in the 5' to 3' direction:
(1) a promoter operably-linked to at least one DNA-binding domain sequence;

(2) a coding sequence or a complement thereof operably-linked to the promoter; and (3) a polyadenylation signal sequence operably-linked to the coding sequence or a complement thereof;

provided that when the promoter is a minimal promoter then the DNA-binding domain sequence is located upstream of the minimal promoter; and (b) a second chimeric gene comprising in the 5' to 3' direction:

(1) a promoter;

(2) a DNA sequence encoding a DNA-binding domain;

(3) a DNA sequence selected from the group consisting of SEQ ID NO:3 and SEQ ID NO:14 operably-linked to the DNA sequence of (2); and (4) a polyadenylation signal sequence operably-linked to the DNA sequence of (3), wherein the expression of the second chimeric gene regulates expression of the first chimeric gene.

Applicants also provide a further method for regulating gene expression in a stably transformed transgenic plant cell which comprises (a) transforming the genome of the plant cell with:

(1) a chimeric gene comprising in the 5 ' to 3' direction:

(i) a promoter operably-linked to at least one DNA-binding domain sequence;

(ii) a coding sequence or a complement thereof operably-linked to the promoter; and (iii) a polyadenylation signal sequence operably-linked to the coding sequence or a complement thereof;

provided that when the promoter is a minimal promoter then the DNA-binding domain sequence is located upstream of the minimal promoter, and (b) infecting the plant produced in (a) with a viral vector comprising:

(1) a promoter;

(2) a DNA sequence encoding a DNA-binding domain;

(3) a DNA sequence selected from the group consisting of SEQ ID NO:3 and SEQ ID NO:14 operably-linked to the DNA sequence of (2); and (4) a polyadenylation signal sequence operably-linked to the DNA sequence of (3);

wherein the expression of the viral vector regulates expression of the chimeric gene of (a). In this method, the preferred DNA-binding domain of (a)(1)(i) is a GAL4 binding domain. Also part of these two method inventions are transformed plants having at least one gene whose expression is regulated using either of these two methods. In the non-viral method, the invention additionally includes seeds obtained from the plants so transformed.

Applicants also provide as part of the invention certain isolated nucleic acids molecules. The isolated nucleic acid molecules encompassed in the invention are those encoding plant MFP1-binding proteins and those encoding plant MAF1-binding proteins.

The invention more specifically encompasses an isolated nucleic acid molecule encoding a plant MFP1-binding protein selected from the group consisting of:

(a) an isolated nucleic acid molecule encoding the amino acid sequence selected from the group consisting of SEQ ID NO:2, SEQ ID NO:4, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35 and SEQ ID NO:37;

(b) an isolated nucleic acid molecule that hybridizes with (a) under the following hybridization conditions: 0.1× SSC, 0.1% SDS at 65° C.; and (c) an isolated nucleic acid molecule that is completely complementary to (a) or (b).

The invention also encompasses the isolated nucleic acid molecule encoding a plant MAF1-binding protein selected from the group consisting of:

(a) an isolated nucleic acid molecule encoding the amino acid sequence selected from the group consisting of SEQ ID NO:9, SEQ ID NO:11, SEQ ID NO:13, SEQ ID NO:15 and SEQ ID NO:17;

(b) an isolated nucleic acid molecule that hybridizes with (a) under the following hybridization conditions: 0.1× SSC, 0.1% SDS at 65° C.; and (c) an isolated nucleic acid molecule that is completely complementary to (a) or (b).

The invention further encompasses the polypeptides respectively encoded by the isolated nucleic acid molecule described above for MPF1-binding protein or by the isolated nucleic acid molecule described above for MAF1-binding protein. The preferred polypeptides are those having at least 50% identity with the amino acid sequences identified by the SEQ ID NOs 2 and 4 for the MPF1-binding protein and having at least 95% identity with the amino acid sequences identified by the SEQ ID NOs specified above for the MAF1-binding protein, respectively.

The invention also encompasses chimeric genes comprising (1) the isolated nucleic acid molecule described above encoding the MPF1-binding protein or by the isolated nucleic acid molecule described above encoding the MAF1-binding protein operably-linked to (2) suitable regulatory sequences. The invention also encompasses host cells transformed with each of the chimeric genes described above. In both cases the host cell is preferably a plant cell or *E. coli*.

Applicants also provide a method of altering the level of expression of binding protein in a host cell comprising:

(a) transforming a host cell with a chimeric gene comprising the isolated nucleic acid molecule described above for either MFP1-binding protein or for MAF1-binding protein, respectively; and (b) growing the transformed host cell of step (a) under conditions that are suitable for expression of particular chimeric gene, resulting in production of altered levels of the particular binding protein in the transformed host cell relative to expression levels of an untransformed host cell.

Applicants further provide a method of obtaining a nucleic acid molecule encoding all or a substantial portion of an amino acid sequence encoding either a MFP1-binding protein or a MAF1-binding protein comprising:

(a) probing a cDNA or genomic library with the nucleic acid molecule described above corresponding to either the MPF1-binding protein or the MAF1-binding protein;

(b) identifying a DNA clone that hybridizes with the nucleic acid molecule used as a probe in (a); and (c) sequencing the cDNA or genomic fragment that comprises the clone identified in step (b), wherein the sequenced cDNA or genomic fragment encodes all or substantially all of the amino acid sequence encoding the particular binding protein. The invention further encompasses the products of this method.

Applicants further provide a method of obtaining a nucleic acid molecule encoding all or a substantial portion of the amino acid sequence encoding either a MFP1-binding protein or a MAF1-binding protein comprising:

(a) synthesizing an oligonucleotide primer corresponding to a portion of (1) the sequence selected from the group consisting of SEQ ID NO:1, SEQ ID NO:3, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34 and SEQ ID NO:36 or (2) the sequence selected from the group consisting of SEQ ID NO:8, SEQ ID NO:10, SEQ ID NO:12, SEQ ID NO:14 and SEQ ID NO:16; and (b) amplifying a cDNA insert present in a cloning vector using the oligonucleotide primer of step (a) and a primer representing sequences of the cloning vector, wherein the amplified cDNA insert encodes a portion of an amino acid sequence encoding a plant MFP1-binding protein or encodes a portion of an amino acid sequence encoding a plant MAF1-binding protein. The invention further includes the products obtained by this method.

Applicants also provide a method for evaluating at least one chemical compound for its ability to inhibit the activity of a plant MFP1-binding protein, comprising the steps of:

(a) contacting at least one chemical compound with a host cell, to form a test system, the host cell comprising:
  (i) a first hybrid protein comprising a first protein fused to a DNA binding domain of a transcriptional activator;
  (ii) a second hybrid protein comprising a second protein fused to an activation domain of a transcriptional activator, and
  (iii) a reporter gene,
wherein the first or second protein is encoded by MFP1, wherein the remaining first or second protein is encoded by the nucleic acid fragment described above encoding a plant MFP1-binding protein and wherein the second hybrid protein binds to the first hybrid protein which allows activation of the reporter gene;

(b) incubating the test system for a suitable time to permit inhibition of the reporter gene;

(c) monitoring the expression of the reporter gene of step (b); and (d) evaluating at least one compound for its ability to inhibit the activity of a plant MFP1-binding protein on the basis of the level of reporter gene expression of step (c).

Furthermore, this evaluation method also encompasses a method for evaluating at least one compound for its ability to inhibit the activity of a plant MAF1-binding protein, comprising the steps of:

(a) contacting at least one chemical compound with a host cell, to form a test system, the host cell comprising:
  (i) a first hybrid protein comprising a first protein fused to a DNA binding domain of a transcriptional activator;
  (ii) a second hybrid protein comprising a second protein fused to an activation domain of a transcriptional activator, and
  (iii) a reporter gene,
wherein the first or second protein is encoded by the nucleic acid moleucle encoding a plant MAF1-binding protein as described above, and wherein the second hybrid protein binds to the first hybrid protein which allows activation of the reporter gene;

(b) incubating the test system for a suitable time to permit inhibition of the reporter gene;

(c) monitoring the expression of the reporter gene of step (b); and (d) evaluating at least one compound for its ability to inhibit the activity of a plant MAF1-binding protein on the basis of the level of reporter gene expression of step (c).

With regard to plant MFP1-binding protein in the evaluation method, the preferred nucleic acid molecule is selected from the group consisting of SEQ ID NO:1, SEQ ID NO:3, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34 and SEQ ID NO:36 and the MFP1-binding protein is selected from the group consisting of SEQ ID NO:2, SEQ ID NO:4, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35 and SEQ ID NO:37. With regard to the plant MAF1-binding protein in the evaluation method, the preferred nucleic acid fragment is selected from the group consisting of SEQ ID NO:8, SEQ ID NO:10, SEQ ID NO:12, SEQ ID NO:14 and SEQ ID NO:16 and the MFP1-binding protein is selected from the group consisting of SEQ ID NO:9, SEQ ID NO:11, SEQ ID NO:13, SEQ ID NO:15 and SEQ ID NO:17.

BRIEF DESCRIPTION OF THE SEQUENCE DESCRIPTIONS

The following sequence descriptions and sequence listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are herein incorporated by reference. The symbols and format used for nucleotide and amino acid sequence data comply with the rules set forth in 37 C.F.R. §1.822. The present invention utilized Wisconsin Package Version 9.0 software from Genetics Computer Group (GCG), Madison, Wis.

SEQ ID NO:1 is the nucleotide sequence of MAF1.

SEQ ID NO:2 is the deduced amino acid sequence of MAF1.

SEQ ID NO:3 is the nucleotide sequence of NMP1.

SEQ ID NO:4 is the deduced amino acid sequence of NMP1.

SEQ ID NO:5 is the consensus sequence for a GAL4 binding site.

SEQ ID NO:6 and SEQ ID NO:7 are the oligonucleotides used to form the GAL4 binding site cassette described in Example 2.

SEQ ID NO:8 is the nucleotide sequence of FLIP1.

SEQ ID NO:9 is the deduced amino acid sequence of FLIP1.

SEQ ID NO:10 is the nucleotide sequence of FLIP2.

SEQ ID NO:11 is the deduced amino acid sequence of FLIP2.

SEQ ID NO:12 is the nucleotide sequence of FLIP3.

SEQ ID NO:13 is the deduced amino acid sequence of FLIP3.

SEQ ID NO:14 is the nucleotide sequence of FLIP4.

SEQ ID NO:15 is the deduced amino acid sequence of FLIP4.

SEQ ID NO:16 is the nucleotide sequence of pD1.

SEQ ID NO:17 is the deduced amino acid sequence of pD1.

SEQ ID NO:18 is the full cDNA sequence in clone cta1n.pk0074.f12 encoding MAF1.

SEQ ID NO:19 is the deduced amino acid sequence of a corn MAF1 derived from the nucleotide sequence of SEQ ID NO:18.

SEQ ID NO:20 is the full cDNA sequence in clone ss1.pk0021.e2 encoding MAF1.

SEQ ID NO:21 is the deduced amino acid sequence of a soybean MAF1 derived from the nucleotide sequence of SEQ ID NO:20.

SEQ ID NO:22 is the full cDNA sequence in clone se1.pk0050.g5 encoding MAF1.

SEQ ID NO:23 is the deduced amino acid sequence of a soybean MAF1 derived from the nucleotide sequence of SEQ ID NO:22.

SEQ ID NO:24 is the nucleotide sequence comprising a portion of the cDNA insert in clone wle1n.pk0104.e10 encoding MAF1.

SEQ ID NO:25 is the deduced amino acid sequence of a wheat MAF1 derived from the nucleotide sequence of SEQ ID NO:24.

SEQ ID NO:26 is the nucleotide sequence comprising a portion of the cDNA insert in clone ect1c.pk001.11 encoding MAF1.

SEQ ID NO:27 is the deduced amino acid sequence of a *Canna edulis* MAF1 derived from the nucleotide sequence of SEQ ID NO:26.

SEQ ID NO:28 is the nucleotide sequence comprising a portion of the cDNA insert in clone pps.pk0009.b7 encoding MAF1.

SEQ ID NO:29 is the deduced amino acid sequence of a *Picramnia pentandra* MAF1 derived from the nucleotide sequence of SEQ ID NO:28.

SEQ ID NO:30 is the full cDNA sequence in clone cbn2.pk0003.a12 encoding NMP1.

SEQ ID NO:31 is the deduced amino acid sequence of a corn NMP1 derived from the nucleotide sequence of SEQ ID NO:30.

SEQ ID NO:32 is the nucleotide sequence comprising a portion of the cDNA insert in clone wr1.pk0025.c2 encoding NMP1.

SEQ ID NO:33 is the deduced amino acid sequence of a wheat NMP1 derived from the nucleotide sequence of SEQ ID NO:32.

SEQ ID NO:34 is the nucleotide sequence comprising a portion of the cDNA insert in clone ph1t.pk0024.h5 encoding NMP1.

SEQ ID NO:35 is the deduced amino acid sequence of a *Phaseolus lunatus* NMP1 derived from the nucleotide sequence of SEQ ID NO:34.

SEQ ID NO:36 is the nucleotide sequence comprising a portion of the cDNA insert in clone bsh1.pk0011.e4 encoding NMP1.

SEQ ID NO:37 is the deduced amino acid sequence of a barley NMP1 derived from the nucleotide sequence of SEQ ID NO:36.

SEQ ID NO:38 is a primer used for the PCR amplification of the NMP1 open reading frame from the plasmid pAD 6-6.

SEQ ID NO:39 is a primer used for the PCR amplification of the NMP1 open reading frame from the plasmid pAD 6-6.

BRIEF DESCRIPTION OF THE BIOLOGICAL DEPOSITS

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| plasmid pZBL1 | ATCC 209128 | 24 June 1997 |

As used herein, "ATCC" refers to the American Type Culture Collection international depository located at 10801 University Boulevard, Manassas, Va., 20110-2209, U.S.A. The "ATCC No." is the accession number to cultures on deposit with the ATCC.

BRIEF DESCRIPTION OF THE DRAWINGS

FIG. 1 shows, by alignment, a comparison of tomato MAF1, a MFP1-binding protein, with 4 other ESTS.

FIG. 2 shows, by alignment, a comparison of tomato NMP1, a MFP1-binding protein, with 6 other ESTS.

DETAILED DESCRIPTION OF THE INVENTION

The instant invention reports the isolation of six proteins that were identified by their ability to either bind to MFP1 or to bind to the MFP1-binding protein MAF1 in a yeast two-hybrid assay. No homologues of these proteins have been described previously in any organism. Five of the six proteins have an alpha-helical structure similar to MFP1 and similar to filament-like proteins from animals and yeast. This structural resemblance to proteins of the cytoskeleton suggests the isolated proteins are part of a nuclear skeleton like the nuclear matrix. In addition, two of the novel proteins (NMP1 and FLIP4) have been shown to activate transcription in yeast, one of them 42% of the strong yeast transcriptional activator GAL4. These proteins can be used to enhance the level of gene expression in plants and other eukaryotic organisms. A two-component gene expression system can be constructed using these proteins, either alone or in combination with already known transcriptional activators. This will allow the expression of novel traits in transgenic plants that can lead to the production of new compounds like food or feed ingredients, pharmaceuticals, or materials, or the suppression of an endogenous plant gene for the purpose of specifically altering the protein composition in the plant. The level of expression of the genes described here can be altered in the plant by methods of cosuppression and overexpression. As they are previously undescribed genes involved in a fundamental cellular mechanism, this can lead to novel developmental phenotypes that might be beneficial for crop growth and development. In addition, if the reduction in expression of one of the genes leads to a growth or developmental defect in the plant, this gene can be used as a novel herbicide target. All isolated proteins can be used as tools to study the plant nuclear matrix, of which no components have been isolated at the molecular level. This can lead to the identification of additional proteins, that can be used as described above. For two of the six proteins (MAF1 and NMP1), EST sequences have been identified, respectively, from MAF1-binding protein for tomato, corn, soybean and wheat, *Canna edulis* and *Picramnia pentandra* and from NMP1-binding protein, from tomato, *Phaselous lunatus,* barley, corn, and wheat, indicating that they are conserved in these crop species. The EST sequences can be directly used for the above described applications in crop plants. All of these sequences can be directly used to broaden our understanding of the mechanisms of MAR-matrix interactions and the molecular basis for the described effects on gene expression.

The following definitions are provided for the full understanding of terms and abbreviations used in this specification.

"Polymerase chain reaction" is abbreviated PCR.
"Expressed sequence tag" is abbreviated EST.
"Open reading frame" is abbreviated ORF.
"SDS polyacrylamide gel electrophoresis" is abbreviated SDS-PAGE.
"Guandidinium hypochloride" is abbreviated GuHCl.
"MFP1-binding factor 1" is abbreviated MAF1.
"Nuclear matrix protein 1" is abbreviated NMP 1.
"Filament-like protein 1" is abbreviated FLIP 1.
"Filament-like protein 2" is abbreviated FLIP2.
"Filament-like protein 3" is abbreviated FLIP3.
"Filament-like protein 4" is abbreviated FLIP4.
"Matrix attachment region" is abbreviated MAR. MARs are also known as matrix-associated regions or scaffold-associated (or attachment) regions.
A "MFP1-binding protein" is a protein that causes activiation of a reporter gene in the yeast two-hybrid assay when cotransformed with MFP1. The definition also encompasses a protein that has more than 50% similarity to a protein that causes activation of a reporter gene in the yeast two-hybrid assay when cotransformed with MFP1.
A "MAF1-binding protein" is a protein that causes activation of a reporter gene in the yeast two-hybrid assay when cotransformed with MAF1.

The terms "isolated nucleic acid fragment" or "isolated nucleic acid molecule" refer to a polymer of RNA or DNA that is single- or double-stranded, optionally containing synthetic, non-natural or altered nucleotide bases. An isolated nucleic acid fragment or an isolated nulceic acid molecule in the form of a polymer of DNA may be comprised of one or more segments of cDNA, genomic DNA, or synthetic DNA.

The terms "host cell" and "host organism" refer to a cell capable of receiving foreign or heterologous genes and expressing those genes to produce an active gene product. Suitable host cells include microorganisms such as bacteria and fungi, as well as plant cells.

The term "fragment" refers to a DNA or amino acid sequence comprising a subsequence of the nucleic acid sequence or protein of the instant invention. However, an active fragment of the instant invention comprises a sufficient portion of the protein to maintain activity.

The term "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides (generally 12 bases or longer) may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

For example, it is well known in the art that antisense suppression and co-suppression of gene expression may be accomplished using nucleic acid fragments representing less than the entire coding region of a gene, and by nucleic acid fragments that do not share 100% identity with the gene to be suppressed. Moreover, alterations in a gene that result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387–395 (1984)), BLASTP, BLASTN, and FASTA (Pearson et al., *Proc. Natl. Acad. Sci. USA* 85:2444–2448 (1988). The BLASTX program is publicly available from NCBI and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990); Altschul et al., "Gapped BLAST and PSI-BLAST: a new generation of protein database search programs", *Nucleic Acids Res.* 25:3389–3402 (1997)). The method to determine percent identity preferred in the instant invention is by the method of DNASTAR protein alignment protocol using the Jotun-Hein algorithm (Hein et al., *Methods Enzymol.* 183:626–645 (1990)). Default parameters used for the Jotun-Hein method for alignments are: for multiple alignments, gap penalty=11, gap length penalty=3; for pairwise alignments ktuple=2. As an illustration, for a polynucleotide having a nucleotide sequence with at least 95% "identity" to a reference nucleotide sequence, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, for a polypeptide having an amino acid sequence having at least 95% identity to a reference amino acid sequence, it is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant tomato proteins as set forth in SEQ ID NO:2, SEQ ID NO:4, SEQ ID NO:9, SEQ ID NO:11, SEQ ID NO:13 and SEQ ID NO:15. The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

The term "complementary" is used to describe the relationship between nucleotide bases that are capable of hybridizing to one another. For example, with respect to DNA, adenosine is complementary to thymine and cytosine is complementary to guanine.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene, not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochemistry of Plants* 15:1–82 (1989)). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably-linked" refers to the association of nucleic acid sequences on a single nucleic acid fragment so that the function of one is affected by the other. For example, a promoter is operably-linked with a coding sequence when it affects the expression of that coding sequence (i.e., that the coding sequence is under the transcriptional control of the promoter). Coding sequences can be operably-linked to regulatory sequences in sense or antisense orientation.

The term "expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth. Enzymol.* 143:277 (1987)) and particle-accelerated or "gene gun" transformation technology (Klein et al., *Nature, London* 327:70–73 (1987); U.S. Pat. No. 4,945,050).

Novel MFP1-binding proteins, MAF1 and NMP1, have been isolated. Comparison of their random cDNA sequences to the GenBank database using the BLAST algorithms, well known to those skilled in the art, revealed that MAF1 and NMP1 are proteins with no significant homologies to other identified proteins. The nucleotide sequences of the MAF1 and NMP1 cDNA are provided in SEQ ID NO:1 and SEQ ID NO:3, and their deduced amino acid sequences are provided in SEQ ID NO:2 and SEQ ID NO:4, respectively.

MAF1 and NMP1 genes from other plants can now be identified by comparison of random cDNA sequences to the MAF1 and NMP1 sequences provided herein.

Novel MAF1-binding proteins, FLIP1, FLIP2, FLIP3 and FLIP4, have been isolated. Comparison of their random cDNA sequences to the GenBank database using the BLAST algorithms, well known to those skilled in the art, revealed that FLIP1, FLIP2, FLIP3 and FLIP4 are proteins with no significant homologies to other identified proteins. The nucleotide sequences of the FLIP1, FLIP2, FLIP3 and FLIP4 cDNA are provided in SEQ ID NO:8, SEQ ID NO:10, SEQ ID NO:12 and SEQ ID NO:14, and their deduced amino acid sequences are provided in SEQ ID NO:9, SEQ ID NO:11, SEQ ID NO:13 and SEQ ID NO:15, respectively. FLIP1, FLIP2, FLIP3 and FLIP4 genes from other plants can now be identified by comparison of random cDNA sequences to the FLIP1, FLIP2, FLIP3 and FLIP4 sequences provided herein.

The nucleic acid fragments of the instant invention may be used to isolate cDNAs and genes encoding a homologous MFP1-binding or MAF1-binding proteins from the same or other plant or fungal species. Isolating homologous genes using sequence-dependent protocols is well known in the art. Examples of sequence-dependent protocols include, but are not limited to, methods of nucleic acid hybridization and methods of DNA and RNA amplification as exemplified by various uses of nucleic acid amplification technologies (e.g., polymerase chain reaction (PCR) or ligase chain reaction).

For example, other MAF1, NMP1, FLIP1, FLIP2, FLIP3 or FLIP4 genes, either as cDNAs or genomic DNAs, could be isolated directly by using all or a portion of the instant nucleic acid fragments as DNA hybridization probes to screen libraries from any desired plant (or fungus) using methodology well known to those skilled in the art. Specific oligonucleotide probes based upon the instant MAF1, NMP1, FLIP1, FLIP2, FLIP3 or FLIP4 sequences can be designed and synthesized by methods known in the art (Maniatis, supra). Moreover, the entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragment may be used in PCR protocols to amplify longer nucleic acid fragments encoding homologous MAF1, NMP1, FLIP1, FLIP2, FLIP3 or FLIP4 genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant MAF1, NMP1, FLIP1, FLIP2, FLIP3 or FLIP4. Alternatively, the second primer sequence may be based upon sequences derived from the cloning vector. For example, the skilled artisan can follow the RACE protocol (Frohman et al., *Proc. Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1: 165 (1989)).

Finally, availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner et al., *Adv. Immunol.* 36:1 (1984); Maniatis, supra).

The nucleic acid fragments of the instant invention may also be used to create transgenic plants in which the instant MAF1, NMP1, FLIP1, FLIP2, FLIP3 or FLIP4 protein is present at higher or lower levels than normal. Alternatively, in some applications, it might be desirable to express the instant MAF1, NMP1, FLIP1, FLIP2, FLIP3 or FLIP4 protein in specific plant tissues and/or cell types, or during developmental stages in which they would normally not be encountered.

Overexpression of the instant MAF1, NMP1, FLIP1, FLIP2, FLIP3 or FLIP4 may be accomplished by first constructing a chimeric gene in which the MAF1, NMP1, FLIP1, FLIP2, FLIP3 or FLIP4 coding region is operably-linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The instant chimeric genes may also comprise one or more introns in order to facilitate gene expression.

Plasmid vectors comprising the instant chimeric genes can then be constructed. The choice of a plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the MAF1, NMP1, FLIP1, FLIP2, FLIP3 or FLIP4 protein to different cellular compartments or to facilitate their secretion from the cell. The chimeric genes described above may be further modified by the addition of appropriate intracellular or extracellular targeting sequence to their coding regions. These include chloroplast transit peptides (Keegstra et al., *Cell* 56:247–253 (1989), signal sequences that direct proteins to the endoplasmic reticulum (Chrispeels et al., *Ann. Rev. Plant Phys. Plant Mol.* 42:21–53 (1991), and nuclear localization signal (Raikhel et al., *Plant Phys.* 100:1627–1632 (1992). While the references cited give examples of each of these, the list is not exhaustive and more targeting signals of utility may be discovered in the future.

It may also be desirable to reduce or eliminate expression of the MAF1, NMP1, FLIP1, FLIP2, FLIP3 or FLIP4 genes in plants for some applications. In order to accomplish this, chimeric genes designed for antisense or co-suppression of MAF1, NMP1, FLIP1, FLIP2, FLIP3 or FLIP4 can be constructed by linking the genes or gene fragments encoding parts of these enzymes to plant promoter sequences. Thus, chimeric genes designed to express antisense RNA for all or part of MAF1, NMP1, FLIP1, FLIP2, FLIP3 or FLIP4 can be constructed by linking the MAF1, NMP1, FLIP1, FLIP2, FLIP3 or FLIP4 genes or gene fragments in reverse orientation to plant promoter sequences. The co-suppression or antisense chimeric gene constructs could be introduced into plants via well known transformation protocols wherein expression of the corresponding endogenous genes are reduced or eliminated.

The instant MAF1, NMP1, FLIP1, FLIP2, FLIP3 or FLIP4 proteins may be produced in heterologous host cells, particularly in the cells of microbial hosts, and can be used to prepare antibodies to the proteins by methods well known to those skilled in the art. The antibodies would be useful for detecting the instant MAF1, NMP1, FLIP1, FLIP2, FLIP3 or FLIP4 protein in situ in cells or in vitro in cell extracts. Preferred heterologous host cells for production of the instant MAF1, NMP1, FLIP1, FLIP2, FLIP3 or FLIP4 protein are microbial hosts. Microbial expression systems and expression vectors containing regulatory sequences that direct high level expression of foreign proteins are well known to those skilled in the art. Any of these could be used to construct a chimeric gene for production of the instant MAF1, NMP1, FLIP1, FLIP2, FLIP3 or FLIP4. This chimeric gene could then be introduced into appropriate microorganisms via transformation to provide high level expression of the instant MAF1, NMP1, FLIP1, FLIP2, FLIP3 or FLIP4 protein.

Microbial host cells suitable for the expression of the instant MAF1, NMP1, FLIP1, FLIP2, FLIP3 or FLIP4 proteins include any cell capable of expression of the chimeric genes encoding these proteins. Such cells will include both bacteria and fungi including, for example, the yeasts (e.g., Aspergillus, Saccharomyces, Pichia, Candida, and Hansenula), members of the genus Bacillus as well as the enteric bacteria (e.g., Escherichia, Salmonella, and Shigella). Methods for the transformation of such hosts and the expression of foreign proteins are well known in the art and examples of suitable protocols may be found in *Manual of Methods for General Bacteriology* (Gerhardt et al., eds., American Society for Microbiology, Washington, D.C. (1994)) or in *Biotechnology: A Textbook of Industrial Microbiology*, Second Edition, Brock, T. D., Sinauer Associates, Inc., Sunderland, Mass. (1989)).

Vectors or cassettes useful for transforming suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although such control regions need not be derived from the genes native to the specific species chosen as a production host.

Initiation control regions or promoters useful to drive expression of the genes encoding the MAF1, NMP1, FLIP1, FLIP2, FLIP3 or FLIP4 proteins in the desired host cell) are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in *E. coli*). Termination control regions may also be derived from various genes native to the preferred hosts. Optionally, a termination site may be unnecessary; however, it is most preferred if included.

Additionally, the instant MAF1, NMP1, FLIP1, FLIP2, FLIP3 or FLIP4 proteins can be used as targets to facilitate the design and/or identification of inhibitors of MAF1, NMP1, FLIP1, FLIP2, FLIP3 or FLIP4 that may be useful as herbicides or fungicides. This could be achieved either through the rational design and synthesis of potent functional inhibitors that result from structural and/or mechanistic information that is derived from the purified instant plant proteins, or through random in vitro screening of chemical libraries. It is anticipated that significant in vivo inhibition of any of the MAF1, NMP1, FLIP1, FLIP2, FLIP3 or FLIP4 proteins described herein may severely cripple cellular metabolism and likely result in plant (or fungal) death.

All or a portion of the nucleic acid fragments of the instant invention may also be used as probes for genetically and physically mapping the genes that they are a part of, and as markers for traits linked to expression of the instant MAF1, NMP1, FLIP1, FLIP2, FLIP3 or FLIP4. Such information may be useful in plant breeding in order to develop lines with desired phenotypes. For example, the instant nucleic acid fragments may be used as restriction fragment length polymorphism (RFLP) markers. Southern blots (Maniatis, supra) of restriction-digested plant genomic DNA may be probed with the nucleic acid fragments of the instant invention. The resulting banding patterns may then be subjected to genetic analyses using computer programs such as Map-Maker (Lander et at., *Genomics* 1:174–181 (1987)) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al., *Am. J. Hum. Genet.* 32:314–331 (1980)).

The production and use of plant gene-derived probes for use in genetic mapping is described by Bernatzky et al. (*Plant Mol. Biol. Reporter* 4:37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., *Nonmammalian Genomic Analysis: A Practical Guide*, pp. 319–346, Academic Press (1996), and references cited therein).

In another embodiment, nucleic acid probes derived from the instant nucleic acid sequence may be used in direct fluorescence in situ hybridization (FISH) mapping.

Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazian et al., *J. Lab. Clin. Med* 114:95–96 (1989)), polymorphism of PCR-amplified fragments (CAPS; Sheffield et al., *Genomics* 16:325–332 (1993)), allele-specific ligation (Landegren et al., *Science* 241:1077–1080 (1988)), nucleotide extension reactions (Sokolov et al., *Nucleic Acid Res.* 18:3671 (1990)), Radiation Hybrid Mapping (Walter et al., *Nature Genetics* 7:22–28 (1997)) and Happy Mapping (Dear et al., *Nucleic Acid Res.* 17:6795–6807 (1989)). For these methods, the sequence of a nucleic acid fragment is used to design and produce primer pairs for use in the amplification reaction or in primer extension reactions. The design of such primers is well known to those skilled in the art. In methods using PCR-based genetic mapping, it may be necessary to identify DNA sequence differences between the parents of the mapping cross in the region corresponding to the instant nucleic acid sequence. This, however, is generally not necessary for mapping methods.

Loss of function-mutant phenotypes may be identified for the instant cDNA clones either by targeted gene disruption protocols or by identifying specific mutants for these genes contained in a maize population carrying mutations in all possible genes (Ballinger et al., *Proc. Natl. Acad. Sci. USA* 86:9402 (1989); Koes et al., *Proc. Natl. Acad. Sci. USA* 92:8149 (1995); Bensen et al., *Plant Cell* 7:75 (1995)). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the MAF1, NMP1, FLIP1, FLIP2, FLIP3 or FLIP4 protein. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a MAF1, NMP1, FLIP1, FLIP2, FLIP3 or FLIP4 protein can be identified and obtained. This mutant plant can then be used to determine or confirm the natural function of the MAF1, NMP1, FLIP1, FLIP2, FLIP3 or FLIP4 gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Standard recombinant DNA and molecular cloning techniques used here are well known in the art and are described by Sambrook, J., Fritsch, E. F. and Maniatis, T. *Molecular Cloning: A Laboratory Manual,* Cold Spring Harbor Laboratory Press, Cold Spring Harbor, 1989 (hereinafter "Maniatis"); and by T. J. Silhavy, M. L. Bennan, and L. W. Enquist, *Experiments with Gene Fusions,* Cold Spring Harbor Laboratory Press, Cold Spring, N.Y. (1984) and by Ausubel et al., *Current Protocols in Molecular Biology,* pub. by Greene Publishing Assoc. and Wiley-Interscience (1987).

Manipulations of genetic sequences were accomplished using the suite of programs available from the Genetics Computer Group Inc. (Wisconsin Package Version 9.0, Genetics Computer Group (GCG), Madison, Wis.).

Table 1 contains a list of the plasmids used in the instant invention.

TABLE 1

Plasmid Summary

| Plasmid | Description |
| --- | --- |
| pRSET A/B/C | Purchased from Invitrogene |
| pBluescript II | All purchased from Stratagene |
| pBD-GAL4 | |
| pGAL4 | |
| pLaminC | |
| p53 | |
| pSV40 | |
| pAD-GAL4 | |
| pAD 6-3 | All phagemids from tomato leaf lambda HybriZAP |
| pAD 6-6 | (Stratagene) cDNA library, all containing Eco RI-Xho I |
| pAD F1 | cDNA inserts in pAD-GAL4 |
| pAD F3 | |
| pAD E2 | |
| pAD I2 | |
| pAD D1 | |
| pAD H2 | |
| pRSET A-8-3 | Pst I/Pvu II fragment of p1-3, containing the 5' half of the MFP1 cDNA and Pvu II/Kpn I fragment of p7-2, containing the 3' half were inserted into pRSET A, digested with Pst I and Kpn I in a 3-way ligation (p1-3, p7-2; Meier et al., Plant Cell 8:2105–2115 (1996)). |
| pBD-MFP1 | Hinc II fragment of 8-3/pRSET A was inserted into unique, filled-in Eco RI site of pBD-GAL4. |
| pBS 6-3 E/X | Eco RI/Xho I fragment of pAD 6-3, containing the MAF1 cDNA, ligated into pBluescript II SK digested with Eco RI/Xho I |
| pBD-MAF1 | Eco RI-Xho I fragment of pBS 6-3 E/X, containing the MAF1 cDNA, inserted into pBD GAL4, digested with Eco RI-Sal I |
| pBS 6-6 E/X | Eco RI/Xho I fragment of pAD 6-6, containing the cDNA of NMP1, inserted into pBluescript II SK, digested with Eco RI/Xho I. |
| pAD 6-6 frame | PCR amplification of the NMP1 open reading frame from the plasmid pAD 6-6 with the primers 5' AGA ATT CGG AAT GGC AGC G 3' (SEQ ID NO:38) and 5' GGA ATT CTC CAA CTC TAG G 3' (SEQ ID NO:39). Eco RI digest of the PCR product, ligation into PAD-GAL4 cut with Eco RI. Sequence was confirmed by complete sequencing of the insert. |
| pBD-NMP1 | The Eco RI fragment of pAD 6-6 frame was inserted into the Eco RI site of pBD GAL4, to create a fusion between the GAL4 DNA-binding domain and NMP1. |
| pRSET C-6-6 | The Bam HI/Kpn I fragment of pBS 6-6 E/X was inserted into pRSET C that had been digested with Bam HI and Kpn I. |
| pBD-D1 | The Eco RI/Xho I fragment from pAD-D1 was inserted into pBD-GAL4 that had been digested with Eco RI and Sal I. |
| pBD-FLIP4 | The Eco RI/Xho I fragment from pAD-12 was inserted into pBD-GAL4 that had been digested with Eco RI and Sal I. |

The meaning of abbreviations is as follows: "sec" means second(s), "min" means minute(s), "h" means hour(s), "d" means day(s), "μL" means microliter, "mL" means Example 1

Isolation of MFP1-Binding Proteins with the Yeast
Two-hybrid Screen

Plant material

Tomato (*Lycopersicon esculentum*) VFNT "cherry" plants were grown under greenhouse conditions. Young tomato leaves (5–10 mm in length) were harvested and frozen in liquid nitrogen. Tobacco (Nicotiana tabacum) Nt-1 suspension culture cells were grown in Nt-1 Medium (1×Murashige and Skoog-salts (Sigma, M-5524), 30 g/L sucrose, 180 mg/L $KH_2PO_4$, 100 mg/L inositol, 1 mg/L thiamine and 2 mg/L 2,4-dichlorophenoxyacetic acid) at 28° C. and constant light on a rotary shaker. 5 mL of cells were subcultured into 95 mL of fresh medium every seven days.

Construction of a Yeast Two-hybrid Library

Poly-$A^+$ RNA was isolated from young tomato leaves using the poly-$A^+$ RNA isolation kit from Pharmacia. A yeast two-hybrid cDNA library was constructed from young fruit poly-$A^+$ RNA using the cDNA synthesis kit, the Gigapack III Gold Packaging extract and the HybriZAP two-hybrid predigested vector kit (all Stratagene, La Jolla, Calif.) according to the manufacturer's protocol. The size of the primary library was determined to be 1.5×106 plaque-forming units. The primary library was amplified according to the manufacturer's protocol and the resulting pAD-GAL4 phagemid library was obtained by in vivo excision. The phagemid library was amplified in *E. coli* XLOLR cells according to the manufacturer's protocol. Plasmid DNA for yeast co-transformation was isolated using the Wizard Maxiprep Kit (Promega, Madison, Wis.).

Construction of the MFP1 Bait

The plasmid pRSET A-8-3 was digested with Hinc II. The 1227 bp Hinc II fragment coding for the amino acids 83–490 of the MFP1 protein was gel-purified and ligated into pBD-GAL4. Prior to ligation pBD-GAL4 was cut with Eco RI and the DNA overhangs were filled in with Klenow polymerase. The correct orientation of the MFP1 fragment and the proper translational fusion were confirmed by restriction analysis and partial sequencing. The MFP1 bait vector was named pBD-MFP1.

Yeast Media

Yeast YRG-2 cells were grown in YPD medium (20 g/L Difco peptone, 10 g/L Difco yeast extract and 2% glucose at pH 5.8 and 30° C.). Transformants were selected on and grown in SD-medium (6.7 g/L Difco yeast nitrogen base without amino acids, 182.2 g/L D-sorbitol and 100 mL/L dropout solution (300 mg/L L-isoleucine, 1500 mg/L L-valine, 200 mg/L L-arginine-hemisulfate, 200 mg/L L-arginine HCl, 200 mg/L L-histidine HCl monohydrate, 1000 mg/L L-leucine, 300 mg/L L-lysine HCl, 200 mg/L L-methionine, 500 mg/L L-phenylalanine, 2000 mg/L L-threonine, 200 mg/L L-tryptophane, 300 mg/L L-tyrosine, 200 mg/L L-uracile and 2% glucose at pH 5.8)), with the amino acid(s) for selection missing.

Yeast Two-hybrid Screen

YRG-2 yeast cells were made competent according to the manufacturer's protocol (Stratagene) and transformed with pBD-MFP1. Transformants were selected on trp dropout plates (SD-T). Transformed cells were made competent, transformed with the two-hybrid library (10 µg DNA) and selected on trp/leu/his dropout plates (SD-LTH). Plasmid DNA was isolated from cells growing on SD-LTH medium and transformed on *E. coli* XL-1 blue. pAD vectors were isolated and cotransformed with pBD-MFP1on YRG-2 yeast cells. Selection was on trp/leu dropout plates (SD-TL). Cotransformants were tested for the expression of the histidine reporter gene by growth on SD-LTH plates. To test for the expression of the lacZ reporter gene, filter lift β-galactosidase assays were performed. Transformed cells were streaked out on SD-LT plates and grown for 3 to 5 days at 30° C. Colonies of 1–2 mm in diameter were transferred to Whatman #1 filter paper and frozen for ca. 10 sec in liquid nitrogen to break open the cells. Filters were thawed at room temperature and transferred to a second Whatman #1 filter placed in a petri dish and soaked with 2.5 mL of Z-buffer (16.1 g/L $Na_2HPO_4 \times 7\ H_2O$, 5.5 g/L $Na_2HPO_4 \times 7\ H_2O$, 0.75 g/L KCl, 0.246 g/L $MgSO_4$, 2.7 mL/L β-mercaptoethanol and containing 16.7 mL/L X-Gal (20 mg/mL in N,N-dimethylformamide)). Plates were incubated at room temperature until blue color developed (0.5–48 h). Plasmids causing the expression of both reporter genes were further investigated.

Characterization of MFP1-binding Factor 1 (MAF1)

The plasmid pAD 6-3 caused activation of both reporter genes in the yeast two-hybrid reporter strain YRG-2 when cotransformed with pBD-MFP1. The 782 bp cDNA was sequenced and contains the complete ORF of a protein which was named MAF1. The protein has a calculated molecular weight of 16.2 kD and an isoelectric point (pI) of 4.2. Northern blot analysis showed that the corresponding mRNA is about 800 nucleotides long, indicating that the isolated cDNA is nearly full-length. It was used in a DNA-hybridization screen to isolate a homologous cDNA from a cDNA library made from young tomato fruits. This homologous cDNA had a longer 5' untranslated region with a stop codon in frame with the predicted start codon, confirming that pAD 6-3 contains the complete ORF of MAF1. The nucleotide sequence of the full-length MAF1 cDNA is provided in SEQ ID NO:1, and the deduced amino acid sequence is provided in SEQ ID NO:2. Database searches (BLAST, Basic Local Alignment Search Tool; Altshul et al. *J. Mol. Biol.* 215,403–410 (1993); see also www.ncbi.nlm.nih.gov/BLAST/) revealed that MAF1 is a novel protein with no significant homologies to other identified proteins.

Characterization of Nuclear Matrix Protein 1 (NMP1)

The plasmid pAD 6-6 caused activation of both reporter genes in the yeast two-hybrid screen when cotransformed with pBD MFP1. The 1301 bp cDNA insert was sequenced and found to contain one long ORF. As the cDNA was not full-length, it was used in a DNA-hybridization screen to isolate a homologous longer cDNA from a cDNA library made from young tomato fruits. This longer cDNA codes for a protein of 330 amino acids that was named NMP1. The nucleotide sequence of the NMP1 cDNA is provided in SEQ ID NO:3, and the deduced amino acid sequence is provided in SEQ ID NO:4. Northern blot analysis showed that the corresponding mRNA is ca. 1300 nucleotides long, confirming that the CDNA is at least near-full length. The ORF continues to the 5' end of the cDNA, but an ATG at position 96 represents a potential start codon with good agreement to the consensus sequence for plant start codons (GGA ATG GCA). In addition, a sequence comparison with the corn NMP1 EST cbn2.pk0003.al2 (see Example 6) shows that the degree of similarity between the two sequences drops significantly upstream of position 96, indicating that this sequence represents 5' untranslated leader sequence. NMP1 is a novel protein that is predominantly alpha helical and has no significant homologies to other identified proteins.

Example 2

Characterization of NMP1 as a Nuclear Matrix-Localized Transcriptional Activator Protein Expression and Purification in *E. coli* and Antibody Production The 1328 bp Bam HI-Kpn I fragment of pBS 6-6 E/X was cloned into the plasmid pRSET C (Invitrogen, San Diego, Calif.) in frame with an N-terminal histidine tag and the 11 amino-acid gene 10 leader peptide (T7 tag) to create pRSET C6-6. Expression of recombinant fusion protein was induced by isopropyl-β-D-thiogalactoside in *E. coli* BL21-DE3 (Novagen) cells, according to the Quiagen protein expression manual (Quiagen, Chatsworth, Netherlands). Proteins were purified by nickel affinity chromatography, as described in the Qiagen protein expression manual. For immunization, proteins were subsequently purified by SDS-polyacrylamide electrophoresis. Antibodies were produced in rabbits by Covance Research Products (Denver, Penn.) using the company's standard immunization protocol.

Nuclear Matrix Localization of NMP1

Total protein extract was prepared from tobacco Nt-1 cells. 100 mg cells were ground in liquid nitrogen to a fine powder, suspended in 1 mL extraction buffer (62.5 mM Tris-HCl pH 6.8, 20% glycerol, 4% SDS and 1.4 M β-mercaptoethanol) and incubated for 10 min at 70° C. After centrifugation at 15,000 rpm for 10 min at 4° C., the supernatant was transferred to a fresh tube, frozen in liquid nitrogen and stored at −80° C. Nuclei and nuclear matrix were isolated from Nt-1 cells according to published teaching (Hall et al., *Proc. Natl. Acad. Sci. USA* 88:9320–9324 (1991)). Equal amounts of protein from total cells, nuclei and nuclear matrix were separated on SDS-PAGE (BioRAD), transferred to a nitrocellulose filter (Hybond-C pure Amersham) and subjected to Western blot analysis with the anti-NMP1 antibody. The results showed that NMP1 is localized in the insoluble nuclear matrix.

Activation of Transcription by NMP1 in Yeast

A plasmid containing the DNA-binding domain of GAL4 in fusion with the complete ORF of NMP1 was constructed by digesting pBS 6-6 with Eco RI and Xho I and ligating the 1295 bp fragment into the vector pBD-GAL4, cut with Eco RI and Sal I, to create pBD-NMP1.

Yeast strain YRG-2 was transformed with the following plasmids and transformed colonies were selected on selective media (SD-T for pBD-NMP1 and pBD-GAL4, SD-L for pGAL4, SD-LT for p53+pSV40 and for pLaminC+pSV40):

Filter Lift β-Galactosidase Assay
    pLaminC+pSV40 (negative control)
    53+pSV40 (positive control)
    pBD-NMP1

ONPG Assay
    pBD-GAL4 (negative control)
    pGAL4 (positive control)
    pBD-NMP1

Colonies were tested for activation of the lacZ gene by β-galactosidase filter lift assays and β-galactosidase activities were quantified by ONPG assays. For filter lift assays transformed cells were streaked out on SD-LT or SD-T plates (see above) and grown for 3 to 5 days at 30° C. Colonies of 1–2 mm in diameter were transferred to Whatman #1 filter paper and frozen for ca. 10 sec in liquid nitrogen to break open the cells. Filters were thawed at room temperature and transferred to a second Whatman #1 filter placed in a petri dish and soaked with 2.5 mL of Z-buffer (16.1 g/L $Na_2HPO_4 \times 7\ H_2O$, 5.5 g/L $Na_2HPO_4 \times 7\ H_2O$, 0.75 g/L KCl, 0.246 g/L $MgSO_4$, 2.7 mL/L β-mercaptoethanol and containing 16.7 mL/L X-Gal (20 mg/mL in N,N-dimethylformamide)). Plates were incubated at room temperature until blue color developed (12–16 h). For ONPG assays cultures were grown overnight in selective media (see above) and diluted to $O.D._{600\ nm}$~0.2 with YPD medium. Cultures were incubated at 30° C. and 300 rpm until an $O.D._{600\ nm}$~0.4–0.7 was reached. 10 mL culture was centrifuged at 4,000 g for 10 min at room temperature and suspended in 0.5 mL Z-buffer. 0.3 mL glassbeads (Sigma G8772, 425–600 nm) were added and the samples were vortexed for 3×3 min, cooling the samples on ice for 1 min at each interval. The samples were centrifuged for 10 min at 15,000 rpm and 4° C., the supernatants were transferred to fresh reaction tubes and stored on ice. The pellets were suspended in 0.5 mL Z-buffer, and the glassbead extraction was repeated as described. The supernatants were combined and 0.75 mL were mixed with 0.16 mL ONPG assay buffer (4 mg/mL ONPG in 0.1 M $NaPO_4$, pH 7.0) and incubated at 30° C. for 100 min. The reactions were stopped by the addition of 0.4 mL 1M $Na_2CO_3$. The yellow color of the reaction product was quantified photometrically at 420 nm. For a blank value, the ONPG assay buffer was incubated for 100 min at 30° C. and used.

β-Galactosidase activity was calculated the following way:

$$U = O.D._{420\ nm} \times 1000 / t \times v \times O.D._{600\ nm}$$

with,
    t=time in min
    v=volume in mL

Table 2 summarizes the results of the ONPG assays. These results (mean values and standard deviation of three samples) show that NMP1 is a strong transcriptional activator in yeast, having about 42% of the strong yeast transcription factor GAL4.

TABLE 2

Activation of Transcription in Yeast by NMP1

| yeast strain | β-galactosidase activity (U) |
| --- | --- |
| YRG-2/pGAL4 | 17.89 +/− 5.15 |
| YRG-2/pBD-GAL4 | 0.25 +/− 0.04 |
| YRG-2/pBD-NMP1 | 7.43 +/− 2.33 |

Activation of Transcription in Plants

A fusion of NMP1 to the DNA-binding domain of GAL4 can be used to activate plant promoters that contain GAL4 binding sites upstream of a plant minimal promoter, such as the phaseolin minimal promoter.

A promoter consisting of four GAL4 binding sites and a phaseolin minimal promoter extending 5' to −65 can be constructed 5' to a β-glucuronidase (GUS) coding region and a phaseolin 3' polyadenylation signal sequence region. The four segments of this chimeric gene called G4G consist of the following:

(1) Oligonucleotides containing four copies of the GAL4 DNA binding site consensus sequence as set forth in SEQ ID NO:5 (Brasselman et al., *Proc. Natl. Acad. Sci., USA* 90:1657 (1993)) and terminal restriction sites. These oligonucleotides have the sequences shown in SEQ ID NO:6 and SEQ ID NO:7.

TCACCGGATCCTACGGAGGACAGTCCTCCGATTTA-
    CGGAGGACAGTCCTCCGAATATCGATAA-
    CGGAGGACAGTCCTCCGATTTACGGAG-
    GACAGTCCTCCGAATTATCTGCAGAATAA (SEQ ID NO:6)

TTATTCTGCAGATAATTCGGAGGACTGTCCTCCG- TAAATCGGAGGACTGTCCTCCGTTATCGATAT- TCGGAGGACTGTCCTCCGTAAATCGGAG- GACTGTCCTCCGTAGGATCCGGTGA (SEQ ID NO:7)

The double-stranded DNA fragment resulting from annealing of these two oligonucleotides has a 5' Bam HI site and a 3' Pst I site.

(2) A Nsi I-Nco I fragment extending from −65 of the phaseolin promoter to +77 with respect to the transcription start site. The Nco I site had been added previously (Slightom et al, *Plant Mol. Biol. Man.* B16:1 (1991)). Pst I and Nsi I ends anneal and ligate without regenerating a restriction site.

(3) A Nco I-Eco RI fragment containing the uida coding region (GUS; Jefferson et al, *EMBO J.* 6:3901 (1987)).

(4) A 1.2 kb Eco RI-Hind III fragment containing the phaseolin polyadenylation signal sequence region (Slightom et al., *Plant Mol. Biol. Man.* B16:1 (1991)). The chimeric G4G gene with Not I and Xba I sites added to the 5' Bam HI site in plasmid pGEM9Zf is called pG4G.

This chimeric gene can be cloned as a Bam HI-Sal I fragment, after addition of the Sal I site 3' to the Hind III site, into the *Agrobacterium tumefaciens* binary vector pZBL1 creating pZBL3. pZBL1 contains the origin of replication from pBR322, the bacterial nptI kanamycin resistance gene, the replication and stability regions of the *Pseudomonas aeruginosa* plasmid pVS1 (Itoh et al., *Plasmid,* 11:206–220 (1984)), T-DNA borders described by van den Elzen et al., (*Plant Mol. Biol.* 5:149–154 (1985)) wherein the OCS enhancer (extending from −320 to −116 of the OCS promoter; Greve et al., *J. Mol. Appl. Genet.* 1:499–511 (1983)) that is a part of the right border fragment is removed, and a Nos/P-nptII-Ocs 3' gene to serve as a kanamycin resistant plant selection marker. Plasmid pZBL1 has been deposited with the ATCC and bears accession number 209128. pZBL1 and pZBL3 can be transformed into *Agrobacterium tumefaciens* LBA4404, which can then be used to inoculate tobacco leaf tissue. Transgenic tobacco plants can be obtained essentially by the procedure of De Blaere et al. (*Meth. Enzymol.* 143:277 (1987)). Selection for transformed shoots can be on 100 mg kanamycin/L. Shoots can be rooted on 100 mg kanamycin/L.

A chimeric protein consisting of the DNA-binding domain of GAL4 (GAL4 BD) and the ORF of NMP1 can be constructed. To do so, the plasmid 35S-G4Alf can be used. 35S-G4Alf contains the Ph/P-G4Alf chimeric activator gene, which has the following four segments: (1) a 494 bp Hind III-Nco I fragment of the phaseolin promoter, extending to −410 and including leader sequences to +77 (Slightom et al. supra), (2) a Nco I-Sma I fragment encoding the N-terminal 147 amino acids of the GAL4 DNA binding domain (Ma et al., *Nature* 334:631 (1988)), (3) a Sma I-Sal I fragment encoding the N terminal 243 amino acids of the PvAlf activation domain (Bobb et al., *Plant J.* 8:101–113 (1995)), and (4) a 1.2 kb Sal I-Hind III fragment containing the phaseolin 3' sequence. In the 35S-G4Alf chimeric activator gene, a 1.4 kb Hind III-Nco I fragment of the 35S promoter and Cab leader was used to replace the −410 phaseolin promoter and leader sequence in the Ph/P-G4Alf chimeric gene. The CaMV 35S promoter+chlorophyll a/b binding protein (cab) leader includes 35S promoter sequences extending to 8 bp beyond (3' to) the transcription start site operably-linked to a 60 bp untranslated leader DNA fragment derived from the cab gene 22L (Harpster et al., *Mol. Gen. Genet.* 212:182 (1988)). The Sma I-Sal I fragment encoding the N terminal 243 amino acids of the PvAlf activation domain (Bobb et al., *Plant J.* 8:101–113 (1995)) can be deleted by digesting the plasmid with Sma I and religating the vector. This results in plasmid p35SCab-G4. In a second step, the Eco RI fragment can be isolated from pAD 6-6 frame and inserted into the single Eco RI site of p35SCab-G4. This will create an in-frame fusion of the N-terminal 147 amino acids of the GAL4 DNA binding domain with the ORF of NMP 1. The resulting plasmid is called p35SCab-G4NMP1.

Leaves of pZBL1 and pZBL3 plants (3 independent transformants each) can be transiently transformed with p35SCab-G4NMP1 by the method of particle gun bombardment as previously described (Baum et al., *Plant J.* 12:463–469 (1997)). Bombarded leaves will be incubated for 2 days at room temperature. β-Glucuronidase activity will be measured as described by Montgomery et al. (*Proc. Natl. Acad. Sci. USA* 90:5939–5943 (1993)).

The gene fusion consisting of the CaMV 35S promoter+ chlorophyll a/b binding protein (cab) leader, the in-frame fusion of the N-terminal 147 amino acids of the GAL4 DNA binding domain with the ORF of NMP1, and the phaseolin 3' sequence can be excised from p35SCab-G4NMP1 and inserted into a binary vector such as pZ5KAD. The binary vector pZ5KAD contains the origin of replication from pBR322, the bacterial kanamycin nptI resistance gene, the replication and stability regions of the Pseudomonas plasmid pVS1 (Itoh et al., supra, T-DNA borders (van den Elzen et al., supra, and a 35S/P-ALS$^R$-ALS 3' gene to serve as a sulfonylurea resistant plant selection marker. The binary vector construction can be transformed into *Agrobacterium tumefaciens* LBA4404, which can then used to inoculate tobacco leaf tissue. Transgenic tobacco plants can be obtained essentially by the procedure of De Blaere et al. supra. Selection for transformed shoots can be on 20–50 ppb chlorsulfuron. Shoots can be rooted on 20 mg chlorsulfuron/l.

Genetic Crossing of Transgenic Tobacco Plants

Primary transformants can be transferred to soil and grown in a growth chamber maintained for a 14 h, 21° C. day, 10 h, 18° C. night cycle, with approximately 80% relative humidity, under mixed cool white fluorescent and incandescent lights. Plants can be grown to maturity and hand pollinations can be performed using a slight modification of the procedure by Wernsman, E. A. and D. F. Matzinger in *Hybridization of Crop Plants* (Fehr, W. R. and Hadley, H. H., eds.), pp 657–668 (1980). Briefly, flowers from plants to be used as the female parents can be selected on the day before anthesis; the corolla can be split longitudinally, the anthers can be removed, and the stigma can be pollinated with pollen from flowers from male parent plants that were allowed to anthese on the plant. To prevent contaminating pollen from reaching the stigma, a 4 cm length of a cocktail stirrer, one end plugged with modeling clay, can be slipped over the stigma and style and held in place by the corolla. Each flower can be tagged. Capsules can be allowed to grow to maturity and then harvested.

Genetic crossing can be conducted at the Ro generation (primary transformants) between the effector plants carrying the chimeric NMP1-GAL4 fusion and the reporter plants carrying a GAL4 binding site promoter-GUS gene. Three independent transgenic tobacco plants containing the reporter gene can be individually crossed to three independent transgenic lines containing the effector gene. The reporter plants can also be crossed to the wild type tobacco plants serving as a control for the gene expression level in the absence of effectors.

Assay of Transgene Expression in Seed $F_1$ seeds from genetic crosses can be analyzed for GUS activities. For each sample about 100 seeds (30 mg) can be quickly frozen in liquid nitrogen and ground in 0.5 mL GUS lysis buffer (50 mM $NaH_2PO_4/Na_2HPO_4$, pH 7, 10 mM EDTA, 0.1% Triton X-100, 0.1% Sarkosyl, 10 mM β-mercaptoethanol). Following a 15 min high speed centrifugation at 4° C., the supernatant can be collected and stored at −70° C. until assayed. For the GUS assay, 25 μL of GUS lysis buffer can be first added into each individual well of a 96-well fluorometric microtitre plate (Titretek Fluoroplate; ICN Biomedicals). One microliter of each sample extract can be added into the 25 μL of GUS lysis buffer in each well. One hundred and fifty microliters of freshly prepared MUG substrate (1.7 mM 4-methylumbelliferyl-β-D-glucuronide (Sigma) in GUS lysis buffer) can be added to each well. The reaction can be stopped by adding 75 μL of 0.6 M $Na_2CO_3$ at 0, 30, 60, and 120 min after addition of MUG substrate. Fluorescence can be detected and quantified using a Perkin-Elmer LS-3B spectrometer. Sample activities can be determined from a standard curve constructed by plotting the amount of MU standards (pmol) versus their measured fluorescence intensities. Protein assays can be performed on the same sample extracts using the Bio-Rad Protein Assay System (Hercules, Calif.) following the manufacturer's instructions for the microtitre plate protocol. GUS activities can then be calculated as pmollmin/mg protein.

Example 3

Isolation and Characterization of MAF1-Binding Proteins

Isolation of MAF1-binding Proteins with the Yeast Two-hybrid Screen

A 729 bp Eco RI-Xho I fragment of pBS 6-3 E/X containing the ORF of the MAF1 cDNA was cloned into pBD-GAL4 digested with Eco RI and Sal I to create pBD-MAF1. Competent YRG-2 yeast cells (Stratagene) were co-transformed with pBD-MAF1 and a two-hybrid cDNA expression library (see Example 1). Transformants were selected on trp/leu/his dropout plates (SD-LTH). Plasmid DNA was isolated from cells growing on SD-LTH medium and transformed on E. coli XL-1 blue. pAD vectors were isolated and co-transformed with pBD-MAF1 on YRG-2 yeast cells. Selection was on trp/leu dropout plates (SD-TL). Cotransformants were tested for the expression of the histidine reporter gene by growth on SD-LTH plates. To test for the expression of the lacZ reporter gene, filter lift β-galactosidase assays were performed. Transformed cells were streaked out on SD-LT plates and grown for 3 to 5 days at 30° C. Colonies of 1–2 mm diameter were transferred to Whatman #1 filter paper and frozen for ca. 10 sec in liquid nitrogen to break open the cells. Filters were thawed at room temperature and transferred to a second Whatman #1 filter placed in a petri dish and soaked with 2.5 mL of Z-buffer (16.1 g/L $Na_2HPO_4 \times 7\ H_2O$, 5.5 g/L $Na_2HPO_4 \times 7\ H_2O$, 0.75 g/L KCl, 0.246 g/L $MgSO_4$, 2.7 mL/L β-mercaptoethanol and containing 16.7 mL/L X-Gal (20 mg/mL in N,N-dimethyl-formamide)). Plates were incubated at room temperature until blue color developed (0.5–48 h). Six plasmids causing the expression of both reporter genes were identified and further investigated.

Characterization of MAF1-binding Proteins

Filament-like Protein 1 (FLIP1)

The plasmid pAD E2 caused activation of both reporter genes in the yeast two-hybrid screen when cotransformed with pBD MAF1. The 1843 bp cDNA insert was sequenced and found to contain one long ORF. It codes for a protein of 525 amino acids (FLIP1). The nucleotide sequence of the FLIP1 cDNA is provided in SEQ ID NO:8, and the deduced amino acid sequence is provided in SEQ ID NO:9. Northern blot analysis showed that the corresponding mRNA is ca 1900 nucleotides long, indicating that the cDNA is at least near-full length. Several ATGs are present in the first 100 bp, but none has good agreement with the plant start site consensus sequence, and the ORF continues to the 5' end of the cDNA. Western blot experiments with an antibody raised against E. coli expressed FLIP1 detects a protein of ca. 45 kD, which is in good agreement with the size of the isolated cDNA, indicating that only a small part of the mRNA sequence might be missing on the cDNA. The protein is present in leaves, fruit, flowers and stems of tomato. FLIP1 is a novel protein that is predominantly alpha helical and has no significant homologies to other identified proteins.

Filament-like Protein 2 (FLIP2)

The plasmid pAD F1 caused activation of both reporter genes in the yeast two-hybrid screen when cotransformed with pBD MAF1. The 2971 bp cDNA insert was sequenced and found to contain one long ORF. It codes for a protein of 843 amino acids (FLIP2). The nucleotide sequence of the FLIP2 cDNA is provided in SEQ ID NO:10, and the deduced amino acid sequence is provided in SEQ ID NO:11. Northern blot analysis showed that the corresponding mRNA is ca 3100 nucleotides long, indicating that the cDNA is at least near full-length. FLIP2 is a novel protein that is predominantly alpha helical and has no significant homologies to other identified proteins Filament-like Protein 3 (FLIP3)

The plasmid pAD F3 caused activation of both reporter genes in the yeast two-hybrid screen when cotransformed with pBD MAF1. The 1945 bp cDNA insert was sequenced and found to contain one long ORF. It codes for a protein of 582 amino acids (FLIP3). The nucleotide sequence of the FLIP3 cDNA is provided in SEQ ID NO:12, and the deduced amino acid sequence is provided in SEQ ID NO:13. Northern blot analysis showed that the corresponding mRNA is ca 2400 nucleotides long, indicating that the cDNA is not full-length, but contains about 80% of the full-length sequence. Western blot experiments with an antibody raised against E. coli-expressed FLIP3 show that the protein is about 100 kD in size and is present in leaves, fruit, flowers and stems of tomato. FLIP3 is a novel protein that is predominantly alpha helical and has no significant homologies to other identified proteins.

Filament-like Protein 4 (FLIP4)

The plasmid pAD 12 caused activation of both reporter genes in the yeast two-hybrid screen when cotransformed with pBD MAF1. The 1562 bp cDNA insert was sequenced and found to contain one long ORF. It codes for a protein of 339 amino acids (FLIP4). The nucleotide sequence of the FLIP4 cDNA is provided in SEQ ID NO:14, and the deduced amino acid sequence is provided in SEQ ID NO:15. Northern blot analysis showed that the corresponding mRNA is ca. 1800–1900 nucleotides long, indicating that the cDNA is not full-length, but contains about 87% of the full-length sequence. Western blot experiments with an antibody raised against E. coli expressed FLIP3 show that the protein is about 47 kD in size and is present in leaves, fruit, and stems of tomato. FLIP4 is a novel protein that is predominantly alpha helical and has no significant homologies to other identified proteins. The plasmids pAD D1 and pAD H2, that also caused activation of both reporter genes in the yeast two-hybrid screen when cotransformed with pBD MAF1, were found to contain shorter versions of the FLIP4 cDNA. The cDNA insert of pAD D1 begins at position 306 of the FLIP4 cDNA. The nucleotide sequence of the pD1 cDNA is provided in SEQ ID NO:16, and the deduced amino acid sequence is provided in SEQ ID NO:17. The cDNA insert of pAD H2 begins at position 348 of the FLIP4 cDNA.

Example 4

Activation of Transcription by FLIP4 in Yeast

Two plasmids containing the DNA-binding domain of GAL4 in fusion with the complete ORF of FLIP4 and a shorter homologous cDNA (pD1) not containing the acidic domain of FLIP4 were constructed in the vector pBD-GAL4. To create pBD-12 the vector pAD-12 was digested with Eco RI and Xho I. The complete cDNA insert was purified on an agarose gel and ligated into pBD-GAL4 digested with Eco RI and Sal I. To create pBD-D1 the vector pAD-D1 was digested with Eco RI and Xho I, the cDNA insert was purified on an agarose gel and ligated into pBD-GAL4 digested with Eco RI and Sal I.

Yeast strain YRG-2 was transformed with pGAL4, pBD-GAL4 and pBD-FLIP4 and transformed colonies were grown on selective media (SD-L for pGAL4 and pBD-GAL4, and SD-T for pBD-FLIP4 and pBD-D1), for 36–48 h, and transferred into YPD media at an $O.D._{600\ nm}$ of 0.2, grown until the $O.D._{600\ nm}$ was between 0.4 to 0.7. Protein extracts were made as described earlier (Example 2). ONPG assays were performed as described (Example 2), except that incubation at 30° C. was for 100 niin. The results are shown in Table 3. The data are expressed as mean value and standard deviation of three independent transformants. The results show that FLIP4 activates transcription in yeast. The activation is about 10% of the activation observed with the yeast transcription factor GAL4. In a second experiment, pGAL4, pBD-FLIP4 and pBD-D1 were transformed onto yeast strain YRG-2 (Table 4). The data show that the N-terminus of FLIP4, containing the acidic domain, is necessary for activation, as pBD-D1 is unable to increase β-galactosidase activity over the value obtained with YRG-2.

TABLE 3

Activation of Transcription in Yeast by FLIP4

| yeast strain | β-galactosidase activity (U) |
| --- | --- |
| YRG-2/pBD-GAL4 | 0.25 +/− 0.04 |
| YRG-2/pGAL4 | 17.89 +/− 5.15 |
| YRG-2/pBD-FLIP4 | 1.8 +/− 0.75 |

TABLE 4

Requirement of the Acidic Domain of FLIP4 for Activation

| yeast strain | β-galactosidase activity (U) |
| --- | --- |
| YRG-2 | 0.025 +/− 0.007 |
| YRG-2/pGAL4 | 1.143 +/− 0.114 |
| YRG-2/pBD-FLIP4 | 0.644 +/− 0.056 |
| YRG-2/pBD-D1 | 0.027 +/− 0.003 |

Example 5

Composition of cDNA Libraries and Identification of cDNA Clones from Other Plant Species Encoding Homologues of MAF1 and NMP1 cDNA libraries representing mRNAs from various plant tissues were prepared. The characteristics of the libraries are described below in Table 4.

TABLE 5 cDNA Libraries from Plants

| Library | Tissue |
| --- | --- |
| cta1n | Corn (*Zea mays*) tassel; normalized from cta1 library* |
| ss1 | Soybean (*Glycine max*) seedling 5–10 day |
| se1 | Soybean (*Glycine max*) embryo, 6–10 DAF |
| wle1n | Wheat (*Triticum aestivum*) leaf seven day old etiolated seedling* |
| ect1c | *Canna edulis* tubers |
| pps | developing seeds of *Picramnia pentandra* (Florida bitterbush) |
| cbn2 | Corn (*Zea mays*) developing kernel two days after pollination |
| wr1 | Wheat (*Triticum aestivum*) root; seven day old seedling, light grown |
| plht | *Phaseolus lunatus* leaf - heat tolerant |
| bsh1 | Barley sheath; developing seedling |

*These libraries were normalized essentially as described in U.S. Pat. No. 5,482,845.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams et al., *Science* 252:1651 (1991)). The resulting ESTs were analyzed using a Perkin Elmer Model 377 fluorescent sequencer.

Figure 1A:
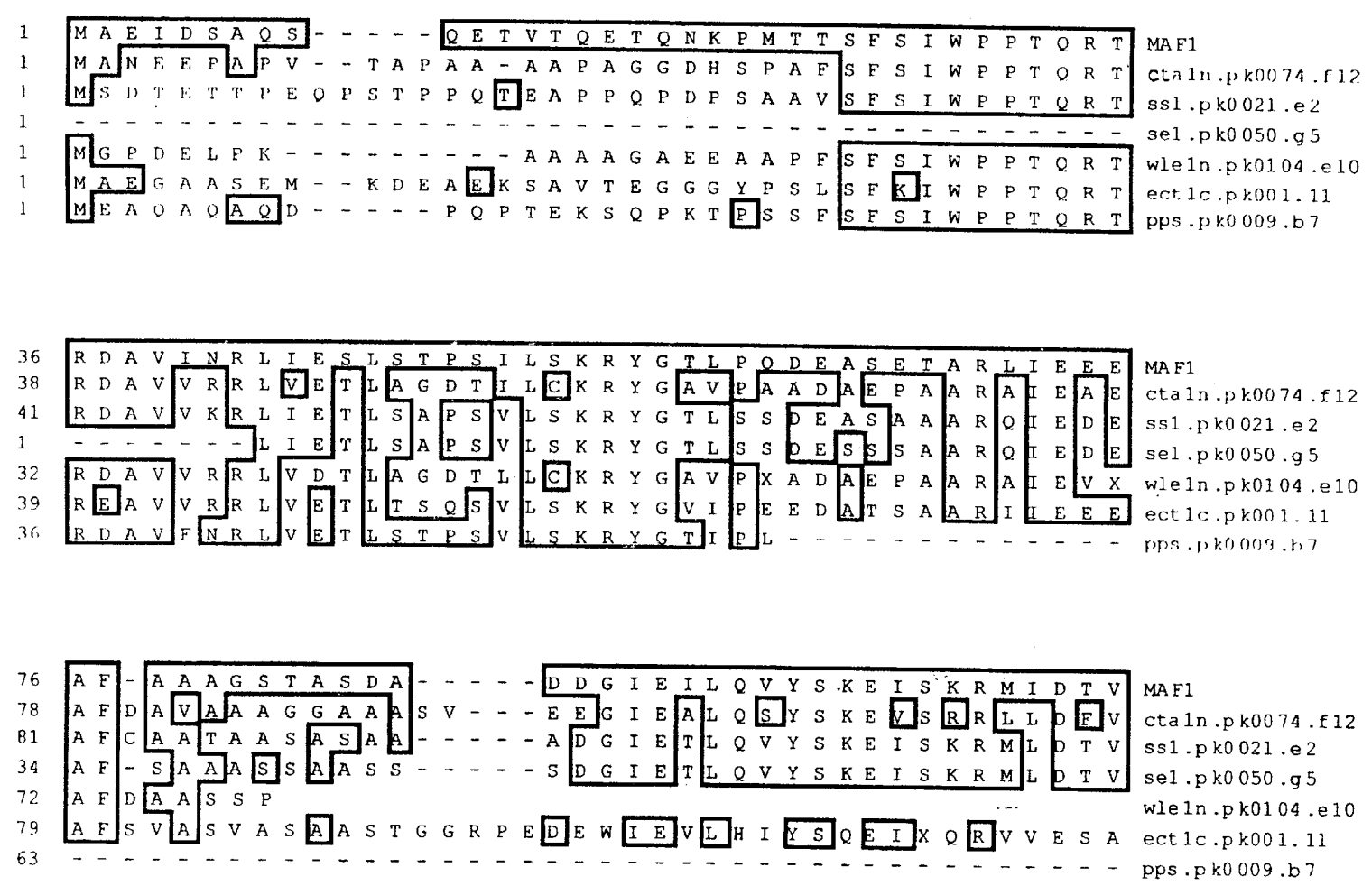
Figure 2A:
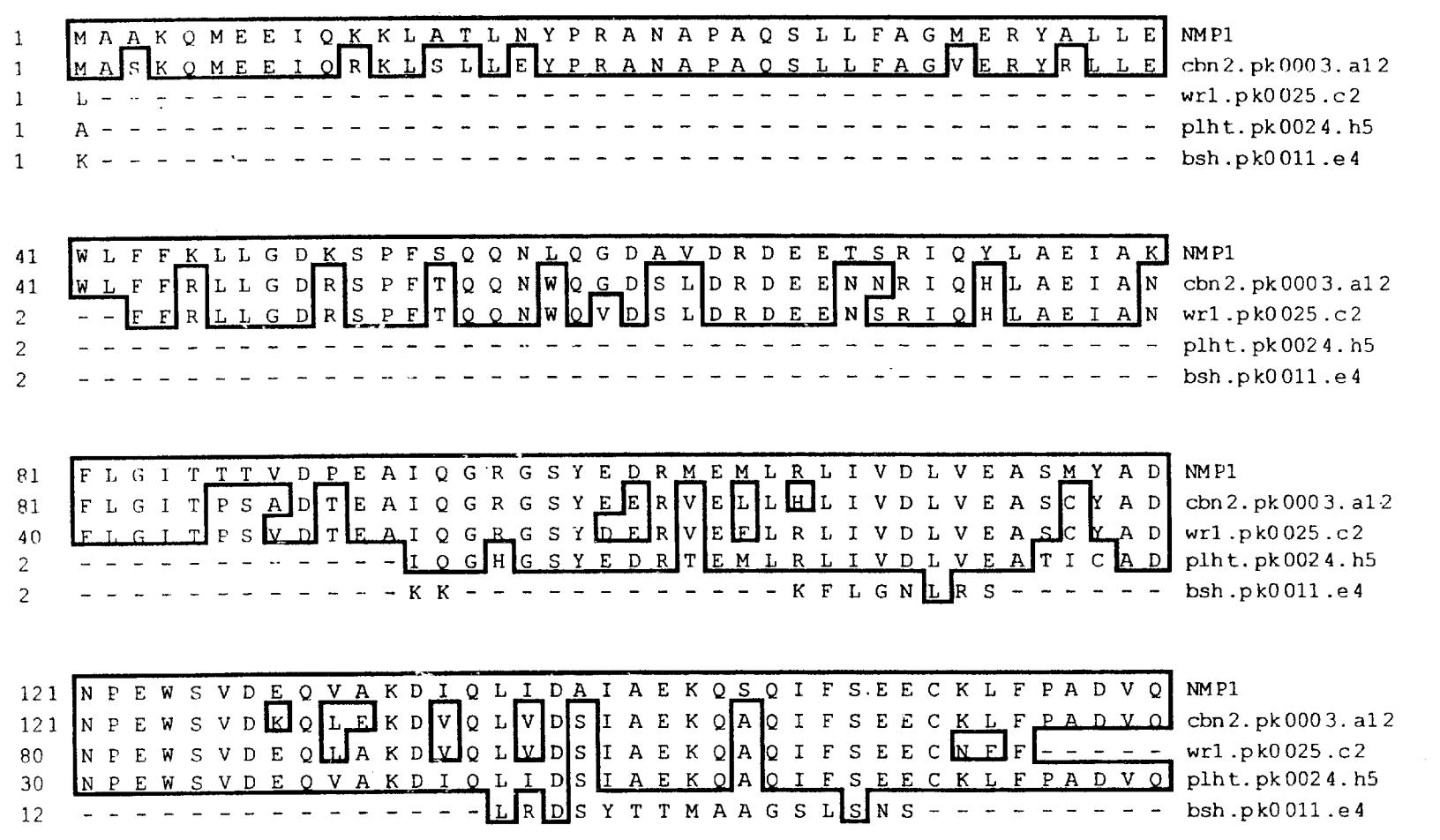
Figure 2B:
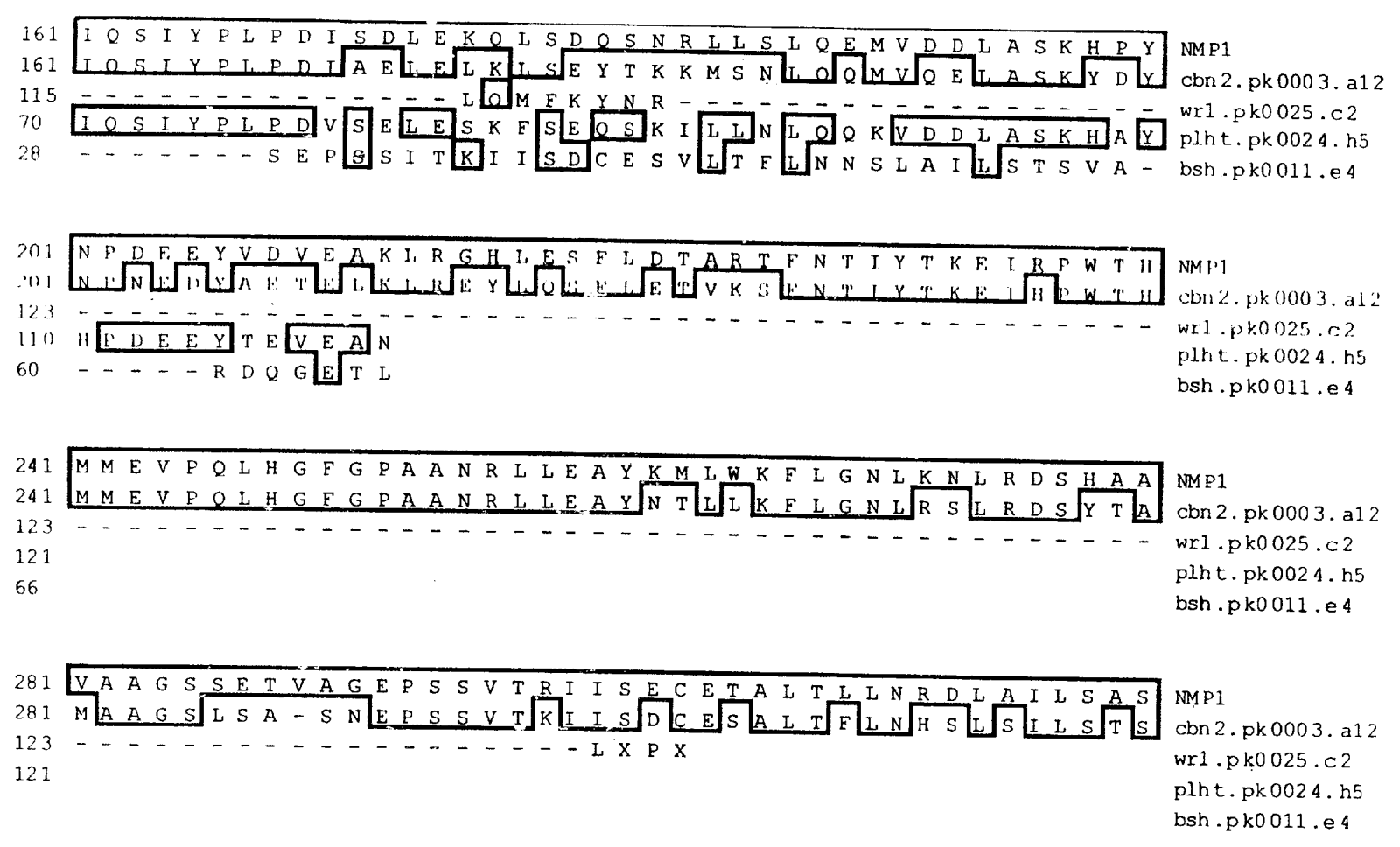

Plant ESTs with similarity to tomato MAF1 and NMP1 were identified by conducting BLAST (Basic Local Alignment Search Tool; Altschul et al., supra; see also www.ncbi.nlm.nih.gov/BLAST/) searches for similarity to sequences contained in the libraries listed in Table 5. Percent identity was determined by the method of DNASTAR protein alignment protocol using the Jotun-Hein algorithm (Hein et al., supra). Default parameters used for the Jotun-Hein method for alignments were: for multiple alignments, gap penalty=11, gap length penalty=3; for pairwise alignments ktuple=2. The EST DNA sequences were translated in all 6 reading frames and compared to the amino acid sequences of the tomato MAF1 and NMP1 cDNAs. ESTs scoring greater than 40% similarity of amino acid sequence were considered similar to tomato cDNAs. Full-insert sequences were obtained for selected ESTs. Table 6 summarizes the identified ESTs and cDNAs and their similarities to the tomato sequences. FIGS. 1 and 2 set out the comparisons in fill for MAF1 and NMP1, respectively. The alignments were done in Megalign (part of the DNASTAR package) using the CLUSTAL algorithm with the default parameters of gap penalty=10 and gap length penalty=10. Also, decoration=box residues that match MAF1 INMP1, respectively.

TABLE 6

ESTs and Full-length cDNAs with Similarity to Tomato MAF1 and NMP1

| tomato cDNA | cDNA clone | organism | full insert/ full-length | % similarity (aa sequence) |
|---|---|---|---|---|
| MAF1 | cta1n.pk0074.f12 | corn | yes/yes | 48 |
|  | ss1.pk0021.e2 | soybean | yes/yes | 60 |
|  | se1.pk0050.g5 | soybean | yes/no | 64 |
|  | wle1n.pk0104.e10 | wheat | no/yes | 47 |
|  | ect1c.pk001.11 | Canna edulis | no/yes | 39 |
|  | pps.pk0009.b7 | Picramnia pentandra | no/yes | 57 |
| NMP1 | cbn2.pk0003.a12 | corn | yes/yes | 73 |
|  | wr1.pk0025.c2 | wheat | no/no | 72 |
|  | plht.pk0024.h5 | Phaseolus lunatus | no/no | 80 |
|  | bsh1.pk0011.e4 | barley | no/no | 58 |

The sequence of the cDNA insert from clone cta1n.pk0074.f12 is shown in SEQ ID NO:18; the deduced amino acid sequence of the cDNA is shown in SEQ ID NO:19. The sequence of the cDNA insert from clone ss1.pk0021.e2 is shown in SEQ ID NO:20; the deduced amino acid sequence of the cDNA is shown in SEQ ID NO:21. The sequence of the cDNA insert from clone se1.pk0050.g5 is shown in SEQ ID NO:22; the deduced amino acid sequence of the cDNA is shown in SEQ ID NO:23. The sequence of a portion of the cDNA insert from clone wle1n.pk0104.e10 is shown in SEQ ID NO:24; the deduced amino acid sequence of the cDNA is shown in SEQ ID NO:25. The sequence of a portion of the cDNA insert from clone ect1c.pk001.11 is shown in SEQ ID NO:26; the deduced amino acid sequence of the cDNA is shown in SEQ ID NO:27. The sequence of a portion of the cDNA insert from clone pps.pk0009.b7 is shown in SEQ ID NO:28; the deduced amino acid sequence of the cDNA is shown in SEQ ID NO:29. The sequence of the cDNA insert from clone cbn2.pk0003.a12 is shown in SEQ ID NO:30; the deduced amino acid sequence of the cDNA is shown in SEQ ID NO:31. The sequence of a portion of the cDNA insert from clone wr1.pk0025.c2 is shown in SEQ ID NO:32; the deduced amino acid sequence of the cDNA is shown in SEQ ID NO:33. The sequence of a portion of the cDNA insert from clone ph1t.pk0024.h5 is shown in SEQ ID NO:34; the deduced amino acid sequence of the cDNA is shown in SEQ ID NO:35. The sequence of a portion of the cDNA insert from clone bsh1.pk0011.e4 is shown in SEQ ID NO:36; the deduced amino acid sequence of the cDNA is shown in SEQ ID NO:37.

What is claimed is:

1. An isolated nucleic acid molecule encoding a plant MFP1-binding protein selected from the group consisting of:
   (a) an isolated nucleic acid molecule encoding a plant MFP1-binding protein having the amino acid sequence selected from the group consisting of SEQ ID NO:2, SEQ ID NO:4, and SEQ ID NO:19;
   (b) an isolated nucleic acid molecule encoding a plant MFP1-binding protein, wherein said nucleic acid molecule hybridizes with (a) under the following hybridization conditions: 0.1×SSC, 0.1% SDS at 65° C.; and
   (c) an isolated nucleic acid molecule encoding a plant MFP1-binding protein, wherein said nucleic acid molecule is completely complementary to (a) or (b).

2. The isolated nucleic acid molecule of claim 1 selected from the group consisting of SEQ ID NO:1, SEQ ID NO:3, and SEQ ID NO:18.

3. The isolated nucleic acid molecule encoding a plant MFP1-binding protein of claim 1, wherein the plant is selected from the group consisting of tomato, and corn.

4. A chimeric gene comprising the isolated nucleic acid molecule of claim 1 operably-linked to suitable regulatory sequences.

5. A transformed host cell comprising the chimeric gene of claim 4.

6. The transformed host cell of claim 5 wherein the host cell is a plant cell.

7. The transformed host cell of claim 5 wherein the host cell is a *E. coli*.

8. A method of altering the level of expression of a MFP1-binding protein in a host cell comprising:
   (a) transforming a host cell with the chimeric gene of claim 4; and
   (b) growing the transformed host cell of step (a) under conditions that are suitable for expression of the chimeric gene, resulting in production of altered levels of a plant MFP1-binding protein in the transformed host cell relative to expression levels of an untransformed host cell.

* * * * *

SEQUENCE LISTING

<160> NUMBER OF SEQ ID NOS: 39

<210> SEQ ID NO 1
<211> LENGTH: 782
<212> TYPE: DNA
<213> ORGANISM: Lycopersicon esculentum

<400> SEQUENCE: 1

```
ccatttcccc aattacccac aaatcacaat tttcaatttc agcgtaaccc tacaaacccc       60
ctcaccgcta ctccaccgca ccaccaccac cgatggcgga aatcgattca gctcagtccc      120
aagagaccgt cactcaggag actcagaaca aaccaatgac cacttccttc agcatttggc      180
caccaactca gcgcactcgt gacgcggtca tcaaccgcct catcgagtct ctgtcaacac      240
cttccattct ctcaaaacgt tatggaactc tcccgcaaga cgaggcatct gaaactgcaa      300
ggttgattga ggaggaggca tttgctgctg ctggatccac tgctagcgat gccgatgacg      360
gcattgagat acttcaggtt tactcaaagg agattagcaa gcgcatgatt gacactgtta      420
agtccagatc tgctcctgct gctgcttcgg agggtgaaag taagccgtcg gagttaccgg      480
ctgatgcttc ggagccttcc tctgcttctg gtctcactgg agaggtctca tccgttgaaa      540
ccgagccttg aagaggtcat ttgctttctt ttgttttgtt aaatatttcc ttctgcagtg      600
agagatcatc taggctttgg ttaattcaat tacttgcaag ctgtattaac tcagataaca      660
gctttatgca gtttatggat tgttaaggtg tttaaatgtt atgttagata tcatgaaatt      720
gatgctatct aaatgaggtt gatggaaaaa gttgtgattt tggcaaaaaa aaaaaaaaaa      780
aa                                                                     782
```

<210> SEQ ID NO 2
<211> LENGTH: 152
<212> TYPE: PRT
<213> ORGANISM: Lycopersicon esculentum

<400> SEQUENCE: 2

```
Met Ala Glu Ile Asp Ser Ala Gln Ser Gln Glu Thr Val Thr Gln Glu
 1               5                  10                  15

Thr Gln Asn Lys Pro Met Thr Thr Ser Phe Ser Ile Trp Pro Pro Thr
             20                  25                  30

Gln Arg Thr Arg Asp Ala Val Ile Asn Arg Leu Ile Glu Ser Leu Ser
         35                  40                  45

Thr Pro Ser Ile Leu Ser Lys Arg Tyr Gly Thr Leu Pro Gln Asp Glu
     50                  55                  60

Ala Ser Glu Thr Ala Arg Leu Ile Glu Glu Ala Phe Ala Ala Ala
 65              70                  75                  80

Gly Ser Thr Ala Ser Asp Ala Asp Gly Ile Glu Ile Leu Gln Val
                 85                  90                  95

Tyr Ser Lys Glu Ile Ser Lys Arg Met Ile Asp Thr Val Lys Ser Arg
             100                 105                 110

Ser Ala Pro Ala Ala Ala Ser Glu Gly Glu Ser Lys Pro Ser Glu Leu
             115                 120                 125

Pro Ala Asp Ala Ser Glu Pro Ser Ser Ala Ser Gly Leu Thr Gly Glu
         130                 135                 140

Val Ser Ser Val Glu Thr Glu Pro
145                 150

<210> SEQ ID NO 3
<211> LENGTH: 1310
<212> TYPE: DNA
<213> ORGANISM: Lycopersicon esculentum

<400> SEQUENCE: 3
ctttcttacc aaattcaaac tctttctctc tcgtctttga gttttcgcca gtaaattctg     60
aagcccaatt gcgaaggaca cgatcgaatt tgggaatggc agcgaaacaa atggaagaaa    120
tacagaagaa attggctaca ttgaattacc aagagccaa tgctcctgct cagtcccttc    180
tctttgccgg catggagcga tacgctcttc ttgaatggct tttcttcaag ttattagggg    240
ataagtcgcc attttctcag caaaatctac aaggggatgc tgtggatcgc gatgaggaga    300
cttcccgcat tcagtattta gcagagattg caaagtttct aggcataact actactgttg    360
atccagaagc aatccaagga cggggtagtt acgaagatcg tatggaaatg ctacgtctta    420
ttgtggatct tgtggaggca agcatgtatg ctgataaccc tgaatggagt gtggatgaac    480
aggtggcaaa agatattcaa ttgattgatg ccatagctga aaagcagtct caaatttttt    540
cagaagaatg caaactgttt cctgcggacg ttcaaatcca gtctatctat cctttgccag    600
acatatctga tttggagaag caactttcag atcaatcaaa taggcttctg agtcttcagg    660
aaatggttga tgatttagca tcaaagcatc catacaaccc agatgaggaa tatgtagatg    720
ttgaagcaaa actacgggga catttggaat ccttttaga cactgcaagg accttcaata    780
caatctatac taaggaaata cgtccatgga cccacatgat ggaagtacca caattgcatg    840
ggtttgggcc agctgccaat agactactgg aagcatataa gatgctctgg aagttcttag    900
ggaacttgaa gaatcttcgg gattcacatg cagctgtagc tgctggttcc tctgaaacag    960
tggctggcga gccatcttcc gtgacaagaa taatctccga atgtgaaact gcacttacac   1020
tcttgaatcg cgatcttgcg attctttcag cttctattgc ccgtgagcga ggtgaagata   1080
tatctttata atttatatgt gacctagagt tggagctaat tgcgtttaca ctatttgttg   1140
ttcttgtaaa atcacatcac attggttgtt agctgttcgc tggtcatgtg tcaaaaatga   1200
```

```
ggagttttca gttaaattgt tgtgttgtgc acgagtaaca aaggcttgtg atatttgtat    1260
ctaattaatc aaagagttct caaaaaaaaa aaaaaaaaa aaaaaaaaa                 1310
```

<210> SEQ ID NO 4
<211> LENGTH: 331
<212> TYPE: PRT
<213> ORGANISM: Lycopersicon esculentum

<400> SEQUENCE: 4

```
Met Ala Ala Lys Gln Met Glu Glu Ile Gln Lys Lys Leu Ala Thr Leu
 1               5                  10                  15

Asn Tyr Pro Arg Ala Asn Ala Pro Ala Gln Ser Leu Leu Phe Ala Gly
             20                  25                  30

Met Glu Arg Tyr Ala Leu Leu Glu Trp Leu Phe Phe Lys Leu Leu Gly
         35                  40                  45

Asp Lys Ser Pro Phe Ser Gln Gln Asn Leu Gln Gly Asp Ala Val Asp
     50                  55                  60

Arg Asp Glu Glu Thr Ser Arg Ile Gln Tyr Leu Ala Glu Ile Ala Lys
 65                  70                  75                  80

Phe Leu Gly Ile Thr Thr Val Asp Pro Glu Ala Ile Gln Gly Arg
                 85                  90                  95

Gly Ser Tyr Glu Asp Arg Met Glu Met Leu Arg Leu Ile Val Asp Leu
            100                 105                 110

Val Glu Ala Ser Met Tyr Ala Asp Asn Pro Glu Trp Ser Val Asp Glu
        115                 120                 125

Gln Val Ala Lys Asp Ile Gln Leu Ile Asp Ala Ile Ala Glu Lys Gln
    130                 135                 140

Ser Gln Ile Phe Ser Glu Cys Lys Leu Phe Pro Ala Asp Val Gln
145                 150                 155                 160

Ile Gln Ser Ile Tyr Pro Leu Pro Asp Ile Ser Asp Leu Glu Lys Gln
                165                 170                 175

Leu Ser Asp Gln Ser Asn Arg Leu Leu Ser Leu Gln Glu Met Val Asp
            180                 185                 190

Asp Leu Ala Ser Lys His Pro Tyr Asn Pro Asp Glu Glu Tyr Val Asp
        195                 200                 205

Val Glu Ala Lys Leu Arg Gly His Leu Glu Ser Phe Leu Asp Thr Ala
    210                 215                 220

Arg Thr Phe Asn Thr Ile Tyr Thr Lys Glu Ile Arg Pro Trp Thr His
225                 230                 235                 240

Met Met Glu Val Pro Gln Leu His Gly Phe Gly Pro Ala Ala Asn Arg
                245                 250                 255

Leu Leu Glu Ala Tyr Lys Met Leu Trp Lys Phe Leu Gly Asn Leu Lys
            260                 265                 270

Asn Leu Arg Asp Ser His Ala Ala Val Ala Ala Gly Ser Ser Glu Thr
        275                 280                 285

Val Ala Gly Glu Pro Ser Ser Val Thr Arg Ile Ile Ser Glu Cys Glu
    290                 295                 300

Thr Ala Leu Thr Leu Leu Asn Arg Asp Leu Ala Ile Leu Ser Ala Ser
305                 310                 315                 320

Ile Ala Arg Glu Arg Gly Glu Asp Ile Ser Leu
                325                 330
```

<210> SEQ ID NO 5
<211> LENGTH: 17
<212> TYPE: DNA

-continued

```
<213> ORGANISM: consensus sequence

<400> SEQUENCE: 5
cggaggacag tcctccg                                                    17

<210> SEQ ID NO 6
<211> LENGTH: 119
<212> TYPE: DNA
<213> ORGANISM: oligonucleotide
<220> FEATURE:
<221> NAME/KEY: protein_bind
<222> LOCATION: (14)..(30)
<223> OTHER INFORMATION: bound_moiety = "GAL4 binding domain"
<220> FEATURE:
<221> NAME/KEY: protein_bind
<222> LOCATION: (36)..(52)
<223> OTHER INFORMATION: bound_moiety = "GAL4 bindng domain"
<220> FEATURE:
<221> NAME/KEY: protein_bind
<222> LOCATION: (64)..(80)
<223> OTHER INFORMATION: bound_moiety = "GAL4 binding domain"
<220> FEATURE:
<221> NAME/KEY: protein_bind
<222> LOCATION: (86)..(102)
<223> OTHER INFORMATION: bound_moiety = "GAL4 binding domain"

<400> SEQUENCE: 6
tcaccggatc ctacggagga cagtcctccg atttacggag gacagtcctc cgaatatcga    60
taacggagga cagtcctccg atttacggag gacagtcctc cgaattatct gcagaataa   119

<210> SEQ ID NO 7
<211> LENGTH: 119
<212> TYPE: DNA
<213> ORGANISM: oligonucleotide
<220> FEATURE:
<221> NAME/KEY: protein_bind
<222> LOCATION: (18)..(34)
<223> OTHER INFORMATION: bound moiety = "GAL4 binding domain"
<220> FEATURE:
<221> NAME/KEY: protein_bind
<222> LOCATION: (40)..(56)
<223> OTHER INFORMATION: bound moiety = "GAL4 binding domain"
<220> FEATURE:
<221> NAME/KEY: protein_bind
<222> LOCATION: (68)..(84)
<223> OTHER INFORMATION: bound moiety = "GAL4 binding domain"
<220> FEATURE:
<221> NAME/KEY: protein_bind
<222> LOCATION: (90)..(106)
<223> OTHER INFORMATION: bound moiety = "GAL4 binding domain"

<400> SEQUENCE: 7
ttattctgca gataattcgg aggactgtcc tccgtaaatc ggaggactgt cctccgttat    60
cgatattcgg aggactgtcc tccgtaaatc ggaggactgt cctccgtagg atccggtga   119

<210> SEQ ID NO 8
<211> LENGTH: 1825
<212> TYPE: DNA
<213> ORGANISM: Lycopersicon esculentum

<400> SEQUENCE: 8
atcctctcca ataactaagg ggtttgggtt gaaaaaatgg aaaaggatga agcgggatgc    60
gcagcgccag gatggggata gtagtgttaa cagcggtaag ctgttgaaac ggggtttggc   120
gagtgagttt gctaatgcag aaaaacctgc aacttttgct gtgggaagga tccaaaaaag   180
tgatggatct gtttcatcta cgagtgcagt attcatgaat cctggagttc tgagtgatgg   240
atttggtgta ataggtgact ctggtttggc tatggggcct aatttttattg ctgtatcgga   300
```

-continued

```
atcagagaac agcgaggatc ggagtagtag gtcttctact gcagctagtg ctccaaaggc    360
aaggtatgaa gcacctgtgc accttggtta tccatctgac aagcattggt tgaggagttt    420
gagtgggaag agcttgagcg catcagctca gaaaccacat cagagaaaag gtcgggctga    480
aacttgtaaa aagcctagag gagaaagggg caaaatcgag aaggaaaact ctcattccag    540
catggaatct gactcgcgaa gctctaattt cctctttatg cagggtgact ttgctacaag    600
taatggtaca aaaggtgaaa ggtcaatgaa ctatgatgaa gaatccagtg atgaagctca    660
ggacagagaa aaggccaattg gtgaggaact tggggctggt ctcgagagag gaatgatag    720 ggagtctgaa aatgtgtcaa agaagatct agctgctgaa tctccgtggg atgttaatga    780
agagaagagt gagaatcacg gttcatccac tgatcacgag cctctaacgg aatctatctt    840
caacttccat gctgctcaag aagctcttgc tagtgaaatt cagaaattca agaaatagg    900 gaaagatact aactttggtc attcacttga ggatgttggt ataccttcaa atttcacgtc    960
agatgactca gattttccta gatcaagcac atccgtgctg tcacagaaca gagatggtgc   1020
tcaaagttct cttaactcct tggagtctga agtgtatagc ctaaagcaga atatattact   1080
gttgcaaaac caggttcagg aggcagctga cctggctaaa tccaaggaag caagagttac   1140
tgaacttgaa gccattttaa gtagtagctc aaagagtgaa gaagactac tgaaggtga    1200 gttcgagagt ctcttcagac tgaaaattga agctgaagtt cagtatgtgg cattgtcaac   1260
aacagcacaa aagttgagaa gtgcagcagt atatcaactt accctcttgg aagaacagaa   1320
gacactagct tcagaacaag cacagatggt gcacgtgcta ggagatgccg aagcaaaggc   1380
tgtagtgctc aagacacaaa ccaagaagtt ggaaacttac tgtgaagatt tagcaagcac   1440
tgccgaaaag ctaaagctac agaagaaagt ctgtaagtac agttcgtgtt ttttcataca   1500
gttggtgttg ttggctgttg ttgttggact gtttctgatg cagatatctc ctgatcatgc   1560
tgaacttgta cccacctaat gttagagaag tttctttctc tctcttttt tcttccactc   1620 cctattatca acatcgtcat ccttcaatgt tgaaagttag attagtttgt ttttagatg   1680 tctatagata gctgaaatac ctacttctca ttttgctgag tctgtattca agggtaatca   1740
tagaagatga tccgttttt gcttctgtaa aaggctgtgc actttgaagt taaaaaaaa    1800 aaaaaaaaaa aaaaaaaaaa aaaaa                                       1825
```

<210> SEQ ID NO 9
<211> LENGTH: 525
<212> TYPE: PRT
<213> ORGANISM: Lycopersicon esculentum

<400> SEQUENCE: 9

```
Ser Ser Pro Ile Thr Lys Gly Phe Gly Leu Lys Lys Trp Lys Arg Met
  1               5                  10                  15

Lys Arg Asp Ala Gln Arg Gln Asp Gly Asp Ser Ser Val Asn Ser Gly
             20                  25                  30

Lys Leu Leu Lys Arg Gly Leu Ala Ser Glu Phe Ala Asn Ala Glu Lys
         35                  40                  45

Pro Ala Thr Phe Ala Val Gly Arg Ile Gln Lys Ser Asp Gly Ser Val
     50                  55                  60

Ser Ser Thr Ser Ala Val Phe Met Asn Pro Gly Val Leu Ser Asp Gly
 65                  70                  75                  80

Phe Gly Val Ile Gly Asp Ser Gly Leu Ala Met Gly Pro Asn Phe Ile
                 85                  90                  95
```

```
Ala Val Ser Glu Ser Glu Asn Ser Glu Asp Arg Ser Ser Arg Ser Ser
            100                 105                 110

Thr Ala Ala Ser Ala Pro Lys Ala Arg Tyr Glu Ala Pro Val His Leu
        115                 120                 125

Gly Tyr Pro Ser Asp Lys His Trp Leu Arg Ser Leu Ser Gly Lys Ser
    130                 135                 140

Leu Ser Ala Ser Ala Gln Lys Pro His Gln Arg Lys Gly Arg Ala Glu
145                 150                 155                 160

Thr Cys Lys Lys Pro Arg Gly Glu Arg Val Lys Ile Glu Lys Glu Asn
                165                 170                 175

Ser His Ser Ser Met Glu Ser Asp Ser Arg Ser Ser Asn Phe Leu Phe
            180                 185                 190

Met Gln Gly Asp Phe Ala Thr Ser Asn Gly Thr Lys Gly Glu Arg Ser
        195                 200                 205

Met Asn Tyr Asp Glu Glu Ser Ser Asp Glu Ala Gln Asp Arg Glu Arg
    210                 215                 220

Pro Ile Gly Glu Glu Leu Gly Ala Gly Leu Glu Arg Gly Asn Asp Arg
225                 230                 235                 240

Glu Ser Glu Asn Val Ser Lys Glu Asp Leu Ala Ala Glu Ser Pro Trp
                245                 250                 255

Asp Val Asn Glu Glu Lys Ser Glu Asn His Gly Ser Ser Thr Asp His
            260                 265                 270

Glu Pro Leu Thr Glu Ser Ile Phe Asn Phe His Ala Ala Gln Glu Ala
        275                 280                 285

Leu Ala Ser Glu Ile Gln Lys Phe Lys Glu Ile Gly Lys Asp Thr Asn
    290                 295                 300

Phe Gly His Ser Leu Glu Asp Val Gly Ile Pro Ser Asn Phe Thr Ser
305                 310                 315                 320

Asp Asp Ser Asp Phe Pro Arg Ser Ser Thr Ser Val Leu Ser Gln Asn
                325                 330                 335

Arg Asp Gly Ala Gln Ser Ser Leu Asn Ser Leu Glu Ser Glu Val Tyr
            340                 345                 350

Ser Leu Lys Gln Asn Ile Leu Leu Leu Gln Asn Gln Val Gln Glu Ala
        355                 360                 365

Ala Asp Leu Ala Lys Ser Lys Glu Ala Arg Val Thr Glu Leu Glu Ala
    370                 375                 380

Ile Leu Ser Ser Ser Lys Ser Glu Glu Thr Thr Glu Gly Glu
385                 390                 395                 400

Phe Glu Ser Leu Phe Arg Leu Lys Ile Glu Ala Glu Val Gln Tyr Val
                405                 410                 415

Ala Leu Ser Thr Thr Ala Gln Lys Leu Arg Ser Ala Ala Val Tyr Gln
            420                 425                 430

Leu Thr Leu Leu Glu Glu Gln Lys Thr Leu Ala Ser Glu Gln Ala Gln
        435                 440                 445

Met Val His Val Leu Gly Asp Ala Glu Ala Lys Ala Val Val Leu Lys
    450                 455                 460

Thr Gln Thr Lys Lys Leu Glu Thr Tyr Cys Glu Asp Leu Ala Ser Thr
465                 470                 475                 480

Ala Glu Lys Leu Lys Leu Gln Lys Lys Val Cys Lys Tyr Ser Ser Cys
                485                 490                 495

Phe Phe Ile Gln Leu Val Leu Leu Ala Val Val Gly Leu Phe Leu
            500                 505                 510

Met Gln Ile Ser Pro Asp His Ala Glu Leu Val Pro Thr
```

<210> SEQ ID NO 10
<211> LENGTH: 2952
<212> TYPE: DNA
<213> ORGANISM: Lycopersicon esculentum

<400> SEQUENCE: 10

```
ggaaaatgag aatttgggtg atgagatttt ggaggatttt gaaacatact gggaagatgt      60
taatgaccgc ttaatggtat caaggatggt aagtgactca gtgattaagg ggatagtgag     120
tgcggtggaa caagaggcag ctgagagact agtgactaag gatatggaat tagccaactt     180
gaaggaatat ttgcaatttc atgaaggggg tcttagcaaa actgaacttg aatcttttgg     240
gtcacttatg tcgcagaatg agctagaaag catggatttt cgaaaatgta tgactttatc     300
agatgttttt atggagcatg gtaagatggg agagtttcta gatgggctaa gaagtttggc     360
gaaagatgaa ttcaagaagt tgaagaagag tattgatgag ctcagaggat ccaattctgt     420
tagtaacaag atctctcgct ctgagatggc gaaactagaa ggtattctac aggaaaaga      480
atctggaatt tgggttcagt tggacaaaac actagacaac ataagaatga tggtggacac     540
cgtctttaaa cgtatggatg ttatgctaca gttgtccaag acatcacttc atcactggca     600
ggaggaacat ctaatcaaag tggagcttga gtccatggta atgcagtgtg taattcggac     660
cgtgcaagaa gaatttgagt acaaactgtg ggaccagtat gctcaattat gtggtgaccg     720
aaatgagaag ttgaatgcca tctctagttt acggacggag ttggatgctg ttttgaagtc     780
attgtcaagt tcagaaaatg ggcatgtgac ttcccatgga tcgcatgatg cagatttctt     840
tacacgcaag aaatcaagtg agtacgtgac ttctaccaaa tcagtttggg atggaaatgg     900
aaagctggag gattctaaga ctgatatacc tgagaatttt gatgctgtca cgttgaagca     960
catgtcaaaa gatgaaatgg tgacctattt taataatata atgacaaaga tgaagagaca    1020
ccatgagtcc attctgcaaa agaaaaccga tgaatatttt gttctaaggg cagagtattt    1080
aaatcttaga ggtggctctg ttgtgcctca taaaaaggat aagggtgaat ctgacattct    1140
aaggaagaag attccagaaa ttatattcaa attggatgat attctggtag agaatgaaaa    1200
acatcctgca tttacccagg agactctaag tttcggtaac ttaaaggata ggcttgataa    1260
ccttctttct gaaaatcacc agcttagaga cttggttaaa gaaaagaaaa atgaagttaa    1320
gtcccttttg tcccaagttt cagatgccac tgagaagagg ctgcaacatt ctttggcaga    1380
agcaggcatg ctaaaacaga taggagaact caatttagcc atggaagagt cactgatagg    1440
aggttctgta agggaagacg tgtatacctg ttttctaaga gatctcagtg gcgggggcaag    1500
aaatgaagtt gaggagttaa acttgggatt taatatgatt aatgaaagta atgatactag    1560
tgctggaagt accagaaaaa ttgaaattga agatttagag atggagtgcc tgattatgca    1620
agaaatttgt ggagtgattt ccggtgaagg cattaaggag gctaaagata tgcttaagga    1680
actgtatttg gagcatttga tgaaaaaga aattcgaact ctcttgata caaaacttat    1740
tgagatggaa aacaaattaa aattcgaggt tgaagagaag acagactga tgcagatgga    1800
aaagttagtg aacgagaagg agaagttagc aacagatgca tcagctgctc tagcaaaaga    1860
gagggttcag tctgagcagg ttcgtcaaga gttgaatgct gcgaaagaat ttgcaagtca    1920
acaacaaaca ttagcttctg ggtgcaacaa agaagtaaat gtaataaagg ccagttggc    1980
agaagcagtg gagcgaattg aagtactgaa agaggaggta gcccaattaa atataagtct    2040
tgaggagaag actgaggagt taaagaagc taatcacagg gcaaatatgg tccttgctat    2100
```

-continued

```
ttctgaagag aggcaaactc ttttgtcctc tcttgaatca aaagaaatag cgctaagaaa    2160
gcaggtggaa aaataattg gtaatataaa tgaatcgtca aaaatgattg ctgattttga     2220 atgcaggtg acaggaaggt tgaaaacaaa taatgcaagg tttgagcact cgttttctca     2280
aatggattgt cttgttaaga aggccaattt gctgagaaga acaacactac tgtatcaaca    2340
aaggcttgaa aaacgatgtt cagaccttaa attggctgag gctgaggttg atcttttggg    2400
agatgaggtg gatacacttc taagcctagt tgagaagatt tacatagcgc ttgatcatta    2460
ctcgccagtt ttacagcatt atcctgggga ttatggagat tcttaagctg atcaaaaggg    2520
aattaactgg agagtctacc aagctagtaa aatcatctcc tgcttaagat aaagagtcta    2580
attcccggtg ttttttcatt ccaatcctgc tggtcctagt ttgaagttca acacgatgct    2640
agaaaaacag attttagttc agcgggacag acgacatgta gtttgtagca acttgaaata    2700
gcacaaagtt cttgaagttt caactgacct gtcttgtaga gggtgagatc ctagttagtt    2760
ctgtatattg tgtatcatca tcagacagga aaatccccac atcttagttg cagctgtgaa    2820
attttaggta cattttgtca gctttcttgt atatagagaa tcaaaatgta cagcctactt    2880
taggctagtt tagttttatg gaaatccatg tgtttatcat ttttcttta aaagaaaaaa     2940 aaaaaaaaaa aa                                                        2952
```

<210> SEQ ID NO 11
<211> LENGTH: 834
<212> TYPE: PRT
<213> ORGANISM: Lycopersicon esculentum

<400> SEQUENCE: 11

```
Glu Asn Glu Asn Leu Gly Asp Glu Ile Leu Glu Asp Phe Glu Thr Tyr
  1               5                  10                  15

Trp Glu Asp Val Asn Asp Arg Leu Met Val Ser Arg Met Val Ser Asp
                 20                  25                  30

Ser Val Ile Lys Gly Ile Val Ser Ala Val Glu Gln Glu Ala Ala Glu
             35                  40                  45

Arg Leu Val Thr Lys Asp Met Glu Leu Ala Asn Leu Lys Glu Tyr Leu
         50                  55                  60

Gln Phe His Glu Gly Gly Leu Ser Lys Thr Glu Leu Glu Ser Phe Gly
 65                  70                  75                  80

Ser Leu Met Ser Gln Asn Glu Leu Glu Ser Met Asp Phe Arg Lys Cys
                 85                  90                  95

Met Thr Leu Ser Asp Val Phe Met Glu His Gly Lys Met Gly Glu Phe
                100                 105                 110

Leu Asp Gly Leu Arg Ser Leu Ala Lys Asp Glu Phe Lys Lys Leu Lys
            115                 120                 125

Lys Ser Ile Asp Glu Leu Arg Gly Ser Asn Ser Val Ser Asn Lys Ile
        130                 135                 140

Ser Arg Ser Glu Met Ala Lys Leu Glu Gly Ile Leu Gln Glu Lys Glu
145                 150                 155                 160

Ser Gly Ile Trp Val Gln Leu Asp Lys Thr Leu Asp Asn Ile Arg Met
                165                 170                 175

Met Val Asp Thr Val Phe Lys Arg Met Asp Val Met Leu Gln Leu Ser
            180                 185                 190

Lys Thr Ser Leu His His Trp Gln Glu His Leu Ile Lys Val Glu
        195                 200                 205

Leu Glu Ser Met Val Met Gln Cys Val Ile Arg Thr Val Gln Glu Glu
```

-continued

```
            210                 215                 220
Phe Glu Tyr Lys Leu Trp Asp Gln Tyr Ala Gln Leu Cys Gly Asp Arg
225                 230                 235                 240

Asn Glu Lys Leu Asn Ala Ile Ser Ser Leu Arg Thr Glu Leu Asp Ala
                245                 250                 255

Val Leu Lys Ser Leu Ser Ser Ser Glu Asn Gly His Val Thr Ser His
            260                 265                 270

Gly Ser His Asp Ala Asp Phe Phe Thr Arg Lys Lys Ser Ser Glu Tyr
                275                 280                 285

Val Thr Ser Thr Lys Ser Val Trp Asp Gly Asn Gly Lys Leu Glu Asp
            290                 295                 300

Ser Lys Thr Asp Ile Pro Glu Asn Phe Asp Ala Val Thr Leu Lys His
305                 310                 315                 320

Met Ser Lys Asp Glu Met Val Thr Tyr Phe Asn Asn Ile Met Thr Lys
                325                 330                 335

Met Lys Arg His His Glu Ser Ile Leu Gln Lys Lys Thr Asp Glu Tyr
                340                 345                 350

Phe Val Leu Arg Ala Glu Tyr Leu Asn Leu Arg Gly Gly Ser Val Val
            355                 360                 365

Pro His Lys Lys Asp Lys Gly Glu Ser Asp Ile Leu Arg Lys Lys Ile
            370                 375                 380

Pro Glu Ile Ile Phe Lys Leu Asp Asp Ile Leu Val Glu Asn Glu Lys
385                 390                 395                 400

His Pro Ala Phe Thr Gln Glu Thr Leu Ser Phe Gly Asn Leu Lys Asp
                405                 410                 415

Arg Leu Asp Asn Leu Leu Ser Glu Asn His Gln Leu Arg Asp Leu Val
            420                 425                 430

Lys Glu Lys Lys Asn Glu Val Lys Ser Leu Leu Ser Gln Val Ser Asp
            435                 440                 445

Ala Thr Glu Lys Arg Leu Gln His Ser Leu Ala Glu Ala Gly Met Leu
            450                 455                 460

Lys Gln Ile Gly Glu Leu Asn Leu Ala Met Glu Glu Ser Leu Ile Gly
465                 470                 475                 480

Gly Ser Val Arg Glu Asp Val Tyr Thr Cys Phe Leu Arg Asp Leu Ser
                485                 490                 495

Gly Gly Ala Arg Asn Glu Val Glu Glu Leu Asn Leu Gly Phe Asn Met
            500                 505                 510

Ile Asn Glu Ser Asn Asp Thr Ser Ala Gly Ser Thr Arg Lys Ile Glu
            515                 520                 525

Ile Glu Asp Leu Glu Met Glu Cys Leu Ile Met Gln Glu Ile Cys Gly
            530                 535                 540

Val Ile Ser Gly Glu Gly Ile Lys Glu Ala Lys Asp Met Leu Lys Glu
545                 550                 555                 560

Leu Tyr Leu Glu His Leu Asn Glu Lys Glu Ile Arg Thr Ser Leu Asp
                565                 570                 575

Thr Lys Leu Ile Glu Met Glu Asn Leu Lys Phe Glu Val Glu Glu
            580                 585                 590

Lys Asp Arg Leu Met Gln Met Glu Lys Leu Val Asn Glu Lys Glu Lys
            595                 600                 605

Leu Ala Thr Asp Ala Ser Ala Ala Leu Ala Lys Glu Arg Val Gln Ser
            610                 615                 620

Glu Gln Val Arg Gln Glu Leu Asn Ala Ala Lys Glu Phe Ala Ser Gln
625                 630                 635                 640
```

Gln Gln Thr Leu Ala Ser Gly Cys Asn Lys Glu Val Asn Val Ile Lys
            645                 650                 655

Gly Gln Leu Ala Glu Ala Val Glu Arg Ile Glu Val Leu Lys Glu Glu
            660                 665                 670

Val Ala Gln Leu Asn Ile Ser Leu Glu Glu Lys Thr Glu Glu Leu Lys
            675                 680                 685

Glu Ala Asn His Arg Ala Asn Met Val Leu Ala Ile Ser Glu Glu Arg
            690                 695                 700

Gln Thr Leu Leu Ser Ser Leu Gly Ser Lys Glu Ile Ala Leu Arg Lys
705                 710                 715                 720

Gln Val Glu Lys Ile Ile Gly Asn Ile Asn Glu Ser Ser Lys Met Ile
            725                 730                 735

Ala Asp Phe Glu Cys Arg Val Thr Gly Arg Leu Lys Thr Asn Asn Ala
            740                 745                 750

Arg Phe Glu His Ser Phe Ser Gln Met Asp Cys Leu Val Lys Lys Ala
            755                 760                 765

Asn Leu Leu Arg Arg Thr Thr Leu Leu Tyr Gln Gln Arg Leu Glu Lys
            770                 775                 780

Arg Cys Ser Asp Leu Lys Leu Ala Glu Ala Glu Val Asp Leu Leu Gly
785                 790                 795                 800

Asp Glu Val Asp Thr Leu Leu Ser Leu Val Glu Lys Ile Tyr Ile Ala
            805                 810                 815

Leu Asp His Tyr Ser Pro Val Leu Gln His Tyr Pro Gly Asp Tyr Gly
            820                 825                 830

Asp Ser

<210> SEQ ID NO 12
<211> LENGTH: 1927
<212> TYPE: DNA
<213> ORGANISM: Lycopersicon esculentum

<400> SEQUENCE: 12
caaagaagac ttagttaagc agcatgctaa agttgccgaa gaagctatcg caggttggga      60
aaaggcagaa aatgaagttg cagttctaaa gcagcaacta gatgcggctg tgcagcaaaa     120
cttgactttg gaagttcgtg tcagtcatct cgacggtgca ctcaaggaat gtgtcaggca     180
gttgagacaa gcaagagatg agcaagagaa aatgattcaa gacgctatgg cagaaaaaaa     240
tgaaatggaa tctgaaaaaa ctgcacttga gaaacagcta cttaagctcc agacacaagt     300
ggaggctggt aaagctgaaa tgcctacttc tactgatcct gatatccttg tcaggcttaa     360
gtatctagag aaagagaatg cagctctcaa aattgaactt gtctcttgtt cagaagtgtt     420
ggaaattagg actattgaga gggatttgag tactcaagca gcagaaactg ccagcaagca     480
gcagctggaa agcataaaaa aactgaccaa acttgaagtt gagtgtcgaa agctacaggc     540
catggctcgc aaatcatccc cattcaatga tcaacgctcc tctgctgttt catctttcta     600
tgtggactct gtcaccgata gccagtctga cagtggagag cggttaaaca cagttgacaa     660
tgatgccctc aaaatgagta aactggaaac aagagaatat gaaccaagtt gctcaaattc     720
atgggcttca gcactcattg ctgagcttga tcaatttaag aatgaaaagg ccatgcctaa     780
aactcttgct gcctgttcta tagaaatcga tatgatggat gatttcttgg agatggagca     840
acttgctgca ttatctgaaa ctgcaaacaa gacaccttca gtaacttctg atgctgttcc     900
tcatgattct cccaatattg agaaccettt ggcagcagaa tacaattcca tttcacaaag     960

-continued

```
ggtggttgaa ttagaacaaa agctggagaa gattgaagca gagaaagctg aactggagaa      1020
tgctttcaac gagagtcaag atgcccttaa agtgtcctct ttgcagctta aggaaactca      1080
aaccaggttg gaagggctgc agaaggagct agatgtggta aatgagtcaa agagttgct       1140 cgagtttcaa ctctatggca tggaggtaga agcacggaca atgtctgtaa atattgattc      1200
tttgaagacg gaagttgaaa agaaaaaatc tttgtcatca gaaatggaag ctaaatgtca      1260
tgaattggaa aacgacctta gaaaaaaatc ccaggaagct gaagctcagc aaacttctgg      1320
ttcaaatagt gaattgaaaa taaaacagga ggatttagcc gtggctgctg acaagcttgc      1380
agaatgccag aaaacaattg catcccttgg gaaacagcta caatccctag ctactctaga      1440
agatttcctg acagacactg caaatcttcc tggtggagga gcagttgttg ctaaagcagg      1500
aggagaacta tggaagttgc atgtaaacga gacatttacc ccaaaacgtg attctgatcc      1560
taccaaggtt gaggagaatg tgagtcattc tacaaacgaa aatgaagggg aatctccagc      1620
atcttcatct tcatcatcta cttcatccac tactcaggct agcactggca aaagcaaaaa      1680
tggctttggg aagttgtttt ctcggagtaa gagtggagtt ccaactctaa aagttatcga      1740
ggataaataa atagaggaag aatgttgaga aggttggaac ataatttgta aaaggtttat      1800
cagttacatg gctgatcaaa ttctgtttga taagcaaact gtttgcttca atagttatga      1860
tgaatatctt gagaagcttc aaatagcaat agacaccttg aatttaaaaa aaaaaaaaaa      1920
aaaaaaa                                                                1927
```

<210> SEQ ID NO 13
<211> LENGTH: 582
<212> TYPE: PRT
<213> ORGANISM: Lycopersicon esculentum

<400> SEQUENCE: 13

```
Lys Glu Asp Leu Val Lys Gln His Ala Lys Val Ala Glu Glu Ala Ile
  1               5                  10                  15

Ala Gly Trp Glu Lys Ala Glu Asn Glu Val Ala Val Leu Lys Gln Gln
             20                  25                  30

Leu Asp Ala Ala Val Gln Gln Asn Leu Thr Leu Glu Val Arg Val Ser
         35                  40                  45

His Leu Asp Gly Ala Leu Lys Glu Cys Val Arg Gln Leu Arg Gln Ala
     50                  55                  60

Arg Asp Glu Gln Glu Lys Met Ile Gln Asp Ala Met Ala Glu Lys Asn
 65                  70                  75                  80

Glu Met Glu Ser Glu Lys Thr Ala Leu Glu Lys Gln Leu Leu Lys Leu
                 85                  90                  95

Gln Thr Gln Val Glu Ala Gly Lys Ala Glu Met Pro Thr Ser Thr Asp
            100                 105                 110

Pro Asp Ile Leu Val Arg Leu Lys Tyr Leu Glu Lys Glu Asn Ala Ala
        115                 120                 125

Leu Lys Ile Glu Leu Val Ser Cys Ser Glu Val Leu Glu Ile Arg Thr
    130                 135                 140

Ile Glu Arg Asp Leu Ser Thr Gln Ala Ala Glu Thr Ala Ser Lys Gln
145                 150                 155                 160

Gln Leu Glu Ser Ile Lys Lys Leu Thr Lys Leu Glu Val Glu Cys Arg
                165                 170                 175

Lys Leu Gln Ala Met Ala Arg Lys Ser Ser Pro Phe Asn Asp Gln Arg
            180                 185                 190

Ser Ser Ala Val Ser Ser Phe Tyr Val Asp Ser Val Thr Asp Ser Gln
```

```
                195                 200                 205
Ser Asp Ser Gly Glu Arg Leu Asn Thr Val Asp Asn Asp Ala Leu Lys
    210                 215                 220

Met Ser Lys Leu Glu Thr Arg Glu Tyr Glu Pro Ser Cys Ser Asn Ser
225                 230                 235                 240

Trp Ala Ser Ala Leu Ile Ala Glu Leu Asp Gln Phe Lys Asn Glu Lys
                245                 250                 255

Ala Met Pro Lys Thr Leu Ala Ala Cys Ser Ile Glu Ile Asp Met Met
            260                 265                 270

Asp Asp Phe Leu Glu Met Glu Gln Leu Ala Ala Leu Ser Glu Thr Ala
        275                 280                 285

Asn Lys Thr Pro Ser Val Thr Ser Asp Ala Val Pro His Asp Ser Pro
    290                 295                 300

Asn Ile Glu Asn Pro Leu Ala Ala Glu Tyr Asn Ser Ile Ser Gln Arg
305                 310                 315                 320

Val Val Glu Leu Glu Gln Lys Leu Glu Lys Ile Glu Ala Glu Lys Ala
                325                 330                 335

Glu Leu Glu Asn Ala Phe Asn Glu Ser Gln Asp Ala Leu Lys Val Ser
            340                 345                 350

Ser Leu Gln Leu Lys Glu Thr Gln Thr Arg Leu Glu Gly Leu Gln Lys
        355                 360                 365

Glu Leu Asp Val Val Asn Glu Ser Lys Glu Leu Leu Glu Phe Gln Leu
    370                 375                 380

Tyr Gly Met Glu Val Glu Ala Arg Thr Met Ser Val Asn Ile Asp Ser
385                 390                 395                 400

Leu Lys Thr Glu Val Glu Lys Glu Lys Ser Leu Ser Ser Glu Met Glu
                405                 410                 415

Ala Lys Cys His Glu Leu Glu Asn Asp Leu Arg Lys Lys Ser Gln Glu
            420                 425                 430

Ala Glu Ala Gln Gln Thr Ser Gly Ser Asn Ser Glu Leu Lys Ile Lys
        435                 440                 445

Gln Glu Asp Leu Ala Val Ala Asp Lys Leu Ala Glu Cys Gln Lys
    450                 455                 460

Thr Ile Ala Ser Leu Gly Lys Gln Leu Gln Ser Leu Ala Thr Leu Glu
465                 470                 475                 480

Asp Phe Leu Thr Asp Thr Ala Asn Leu Pro Gly Gly Ala Val Val
                485                 490                 495

Ala Lys Ala Gly Gly Glu Leu Trp Lys Leu His Val Asn Glu Thr Phe
            500                 505                 510

Thr Pro Lys Arg Asp Ser Asp Pro Thr Lys Val Glu Glu Asn Val Ser
        515                 520                 525

His Ser Thr Asn Glu Asn Glu Gly Glu Ser Pro Ala Ser Ser Ser Ser
    530                 535                 540

Ser Ser Thr Ser Ser Thr Thr Gln Ala Ser Thr Gly Lys Ser Lys Asn
545                 550                 555                 560

Gly Phe Gly Lys Leu Phe Ser Arg Ser Lys Ser Gly Val Pro Thr Leu
                565                 570                 575

Lys Val Ile Glu Asp Lys
            580

<210> SEQ ID NO 14
<211> LENGTH: 1544
<212> TYPE: DNA
<213> ORGANISM: Lycopersicon esculentum
```

-continued

<400> SEQUENCE: 14

```
tgagccaccg ccggcgcagg cgaatcatat atttatatca ccagcgttgt atataactcc    60
tgaaccagct ccgattccgg agacttcttc tggttcgttg tctccttctc cttatttagt   120
caaccacaag cgacgtggcg gtggagaagc atttgcgaac cggaaacttg atggattgga   180
ggaagctgag caagttaacg gacagactga tttggatttg gatttgaatt tgaatttgga   240
agaggagcta cctgaggaaa atttgtttga ggaagatgag ggattttttgg atccgagatg   300
tgatgcgtta agtgttggta gtgttaatga ggtgaaaggg attgattgcc ggagctatgt   360
gtctgctcaa ggggagttct ttgatgcaga cgaagatttc tccgtggaag ggtcgtctct   420
gaatggatct acatgtggac ctaatattga atgggaactg cgcaccacaa agctcaaatt   480
ccttgaggaa atcgaaagaa gaaaaacagc agaagatgct cttaatatga tgcgatgcca   540
gtggcagaac atcagtactg ttctatctca ggcagggcta acacttcctt ctccttcaga   600
tgtcattggt gatatgcagc ttgataatgc ttcaattgag cagctctatc aggaagtagt   660
tgtctcaaga tttgttgctg aagcaattgg aaaaggtcaa gctcgtgcag aagctgaact   720
agctgcagaa tcagttcttg agtcaaaaaa ccaggaaatt tcaaggttga gagacaggct   780
ccgatactac gaggctgtaa atcacgagat gtcccagaga aatcaggaaa tcattgaggt   840
tgcacggaag cagcgccaga ggaaaaaaat ccagaagaag tggctatgga gttgtatagg   900
gctctctgct gccattggcg tttcagtact ttcttataag tacctgccac aagcaagtaa   960
acatcaacca agttcatacc ccaatgaatc aacaagtact ggcactcaca aaactggcta  1020
acaaaatttg ttaatttgct cagccaacat gcacacatgg ggttttaaga agagttacat  1080
ataggttagg tcttgcggga aaaacatggc tttacgctgc agttttgctc ctctaataaa  1140
agttggatga gctagttaat gtttgtagtt ttaacagttg gtgctggtgc tagatgaaaa  1200
gggttttttgc ttagtgcctg tgcagatcag atttcaattt caaggctgtt aagtgtgctc  1260
acttaataat agtgacctga gttttggatg tactcgatgt tgatatttct gtattgtgta  1320
cagtacagaa ctgggtagat gatgaagcca gatcagttca tgtttgtata cgtcagttag  1380
tcggtaggaa tgatgtacct gcttctatcc tatctgtgat gtaacgtttc tttctattca  1440
gttattaatt taagagaga gatctctgta atgaaaaaaa aaaaaaaaaa aaaaaaaaaa  1500
aaaaaaaaa aaaaaaaaa aaaaaaaaa aaaaaaaaa aaaa                      1544
```

<210> SEQ ID NO 15
<211> LENGTH: 339
<212> TYPE: PRT
<213> ORGANISM: Lycopersicon esculentum

<400> SEQUENCE: 15

```
Glu Pro Pro Ala Gln Ala Asn His Ile Phe Ile Ser Pro Ala Leu
 1               5                  10                  15

Tyr Ile Thr Pro Glu Pro Ala Pro Ile Pro Glu Thr Ser Ser Gly Ser
            20                  25                  30

Leu Ser Pro Ser Pro Tyr Leu Val Asn His Lys Arg Arg Gly Gly Gly
        35                  40                  45

Glu Ala Phe Ala Asn Arg Lys Leu Asp Gly Leu Glu Glu Ala Glu Gln
    50                  55                  60

Val Asn Gly Gln Thr Asp Leu Asp Leu Asp Leu Asn Leu Asn Leu Glu
65                  70                  75                  80

Glu Glu Leu Pro Glu Glu Asn Leu Phe Glu Glu Asp Glu Gly Phe Leu
```

85                  90                  95
Asp Pro Arg Cys Asp Ala Leu Ser Val Gly Ser Val Asn Glu Val Lys
                100                 105                 110
Gly Ile Asp Cys Arg Ser Tyr Val Ser Ala Gln Gly Glu Phe Phe Asp
            115                 120                 125
Ala Asp Glu Asp Phe Ser Val Glu Gly Ser Ser Leu Asn Gly Ser Thr
        130                 135                 140
Cys Gly Pro Asn Ile Glu Trp Glu Leu Arg Thr Thr Lys Leu Lys Phe
145                 150                 155                 160
Leu Glu Glu Ile Glu Arg Arg Lys Thr Ala Glu Asp Ala Leu Asn Met
                165                 170                 175
Met Arg Cys Gln Trp Gln Asn Ile Ser Thr Val Leu Ser Gln Ala Gly
            180                 185                 190
Leu Thr Leu Pro Ser Pro Ser Asp Val Ile Gly Asp Met Gln Leu Asp
        195                 200                 205
Asn Ala Ser Ile Glu Gln Leu Tyr Gln Glu Val Val Val Ser Arg Phe
    210                 215                 220
Val Ala Glu Ala Ile Gly Lys Gly Gln Ala Arg Ala Glu Ala Glu Leu
225                 230                 235                 240
Ala Ala Glu Ser Val Leu Glu Ser Lys Asn Gln Glu Ile Ser Arg Leu
                245                 250                 255
Arg Asp Arg Leu Arg Tyr Tyr Glu Ala Val Asn His Glu Met Ser Gln
            260                 265                 270
Arg Asn Gln Glu Ile Ile Glu Val Ala Arg Lys Gln Arg Gln Arg Lys
        275                 280                 285
Lys Ile Gln Lys Lys Trp Leu Trp Ser Cys Ile Gly Leu Ser Ala Ala
    290                 295                 300
Ile Gly Val Ser Val Leu Ser Tyr Lys Tyr Leu Pro Gln Ala Ser Lys
305                 310                 315                 320
His Gln Pro Ser Ser Tyr Pro Asn Glu Ser Thr Ser Thr Gly Thr His
                325                 330                 335
Lys Thr Gly

<210> SEQ ID NO 16
<211> LENGTH: 1180
<212> TYPE: DNA
<213> ORGANISM: Lycopersicon esculentum

<400> SEQUENCE: 16
gttaagtgtt ggtagtgtta atgaggtgaa agggattgat tgccggagct atgtgtctgc      60
tcaaggggag ttctttgatg cagacgaaga tttctccgtg aagggtcgt ctctgaatgg      120
atctacatgt ggacctaata ttgaatggga actgcgcacc acaaagctca aattccttga      180
ggaaatcgaa agaagaaaaa cagcagaaga tgctcttaat atgatgcgat gccagtggca      240
gaacatcagt actgttctat ctcaggcagg gctaacactt ccttctcctt cagatgtcat      300
tggtgatatg cagcttgata atgcttcaat tgagcagctc tatcaggaag tagttgtctc      360
aagatttgtt gctgaagcaa ttggaaaagg tcaagctcgt gcagaagctg aactagctgc      420
agaatcagtt cttgagtcaa aaaccagga aatttcaagg ttgagagaca ggctccgata      480
ctacgaggct gtaaatcacg agatgtccca gagaaatcag gaaatcattg aggttgcacg      540
gaagcagcgc cagaggaaaa aaatccgaaa gaagtggcta tggagttgta tagggctctc      600
tgctgccatt ggcgtttcag tactttctta taagtacctg ccacaagcaa gtaaacatca      660

-continued

```
accaagttca taccccaatg aatcaacaag tactggcact cacaaaactg gctaacaaaa    720
tttgttaatt tgctcagcca acatgcacac atggggtttt aagaagagtt acatataggt    780
taggtcttgc gggaaaaaca tggctttacg ctgcagtttt gctcctctaa taaaagttgg    840
atgagctagt taatgtttgt agttttaaca gttggtgctg gtgctagatg aaaagggttt    900
ttgcttagtg cctgtgcaga tcagatttca atttcaaggc tgttaagtgt gctcacttaa    960
taatagtgac ctgagttttg gatgtactcg atgttgatat ttctgtattg tgtacagtac   1020
agaactgggt aratgatgaa gccagatcag ttcatgtttg tatacgtcag ttagtcggta   1080
ggaatgatgt acctgcttct atcctatctg tgatgtaacg tttctttcta ttcagtaaaa   1140
aaattaaaga gaaaaaaaac gaagaaaaag gagaaaaaaa                         1180
```

<210> SEQ ID NO 17
<211> LENGTH: 237
<212> TYPE: PRT
<213> ORGANISM: Lycopersicon esculentum

<400> SEQUENCE: 17

```
Leu Ser Val Gly Ser Val Asn Glu Val Lys Gly Ile Asp Cys Arg Ser
  1               5                  10                  15

Tyr Val Ser Ala Gln Gly Glu Phe Phe Asp Ala Asp Glu Asp Phe Ser
                 20                  25                  30

Val Glu Gly Ser Ser Leu Asn Gly Ser Thr Cys Gly Pro Asn Ile Glu
             35                  40                  45

Trp Glu Leu Arg Thr Thr Lys Leu Lys Phe Leu Glu Glu Ile Glu Arg
         50                  55                  60

Arg Lys Thr Ala Glu Asp Ala Leu Asn Met Met Arg Cys Gln Trp Gln
 65                  70                  75                  80

Asn Ile Ser Thr Val Leu Ser Gln Ala Gly Leu Thr Leu Pro Ser Pro
                 85                  90                  95

Ser Asp Val Ile Gly Asp Met Gln Leu Asp Asn Ala Ser Ile Glu Gln
                100                 105                 110

Leu Tyr Gln Glu Val Val Val Ser Arg Phe Val Ala Glu Ala Ile Gly
            115                 120                 125

Lys Gly Gln Ala Arg Ala Glu Ala Glu Leu Ala Ala Glu Ser Val Leu
        130                 135                 140

Glu Ser Lys Asn Gln Glu Ile Ser Arg Leu Arg Asp Arg Leu Arg Tyr
145                 150                 155                 160

Tyr Glu Ala Val Asn His Glu Met Ser Gln Arg Asn Gln Glu Ile Ile
                165                 170                 175

Glu Val Ala Arg Lys Gln Arg Gln Arg Lys Ile Gln Lys Lys Trp
            180                 185                 190

Leu Trp Ser Cys Ile Gly Leu Ser Ala Ala Ile Gly Val Ser Val Leu
        195                 200                 205

Ser Tyr Lys Tyr Leu Pro Gln Ala Ser Lys His Gln Pro Ser Ser Tyr
    210                 215                 220

Pro Asn Glu Ser Thr Ser Thr Gly Thr His Lys Thr Gly
225                 230                 235
```

<210> SEQ ID NO 18
<211> LENGTH: 814
<212> TYPE: DNA
<213> ORGANISM: Zea mays

<400> SEQUENCE: 18

-continued

| | | | | |
|---|---|---|---|---|
| cccccgccat | actccgaccc | tagggtttcc | gtcctcttcc | gtaagcttcc aaaaaaatgg | 60 |
| ccaacgagga | gccggctccc | gtcaccgctc | ctgccgccgc | cgcccagcc ggggcgacc | 120 |
| attctccggc | cttctcgttc | agcatctggc | cgccgacgca | gcgacgcgg gacgcggtgg | 180 |
| tgcggcgcct | cgtggagacg | ctcgcggggg | acaccatcct | ctgcaagcgc tacggcgccg | 240 |
| tgccggccgc | cgacgccgag | cccgcggcgc | gcgccatcga | ggccgaggcc ttcgacgccg | 300 |
| tggccgccgc | gggaggcgcc | gccgcctccg | tggaggaggg | gatcgaggcg ctgcagtcct | 360 |
| actccaagga | ggtgagccgc | cgcctcctcg | actttgtcaa | gtcccgctcc gcggacgcca | 420 |
| aggccgaccc | gccgtcggcg | gaggccctgg | ccctgacgc | gcccgaggcc cagcccgcgg | 480 |
| cgtgagcgcc | ggacagccag | tcgttccgta | cctgatcttc | ctgagatgag attgagtcgc | 540 |
| gtctggagtt | tgtgtggaga | ctgcagcctg | tgtgtgtggc | aaagtctggg tctgtatgac | 600 |
| ttgaacgtta | gctgtttgca | catctatgca | gttcttcttc | cacggatgtc tgatttagtg | 660 |
| cgtgctctta | ttttacttct | tgcaatgact | gcccctgacc | aacgattatg ttccgtttgc | 720 |
| tgtgacgctc | atgcatcagg | cctcgagtga | tagataaatc | cgaaataaca agcagaatcc | 780 |
| tcccatcttt | caagccaaaa | aaaaaaaaaa | aaaa | | 814 |

<210> SEQ ID NO 19
<211> LENGTH: 142
<212> TYPE: PRT
<213> ORGANISM: Zea mays

<400> SEQUENCE: 19

```
Met Ala Asn Glu Glu Pro Ala Pro Val Thr Ala Pro Ala Ala Ala
 1               5                  10                  15

Pro Ala Gly Gly Asp His Ser Pro Ala Phe Ser Phe Ser Ile Trp Pro
            20                  25                  30

Pro Thr Gln Arg Thr Arg Asp Ala Val Val Arg Arg Leu Val Glu Thr
        35                  40                  45

Leu Ala Gly Asp Thr Ile Leu Cys Lys Arg Tyr Gly Ala Val Pro Ala
    50                  55                  60

Ala Asp Ala Glu Pro Ala Ala Arg Ala Ile Glu Ala Glu Ala Phe Asp
65                  70                  75                  80

Ala Val Ala Ala Ala Gly Gly Ala Ala Ser Val Glu Glu Gly Ile
                85                  90                  95

Glu Ala Leu Gln Ser Tyr Ser Lys Glu Val Ser Arg Arg Leu Leu Asp
            100                 105                 110

Phe Val Lys Ser Arg Ser Ala Asp Ala Lys Ala Asp Pro Pro Ser Ala
        115                 120                 125

Glu Ala Leu Ala Pro Asp Ala Pro Glu Ala Gln Pro Ala Ala
    130                 135                 140
```

<210> SEQ ID NO 20
<211> LENGTH: 651
<212> TYPE: DNA
<213> ORGANISM: Glycine max

<400> SEQUENCE: 20

| | | | | |
|---|---|---|---|---|
| taacaatgtc | cgacacggaa | accacgcccg | aacaaccctc | cactccgccg caaacggagg | 60 |
| ctccgccgca | gcccgacccc | tccgccgccg | tctccttcag | catatggccc cccactcagc | 120 |
| gcacccgcga | cgccgtcgtc | aaacgcttga | tcgagaccct | ctccgccccc tccgtcctct | 180 |
| ccaagcgcta | cggcactctc | tcctccgacg | aagcctccgc | cgccgcccga cagatcgagg | 240 |

```
acgaggcctt ctgcgccgcc accgcagcct ccgcttcggc cgccgccgac ggcattgaga      300
ccctccaggt ctactccaag gagatcagca agcggatgct cgacaccgtc aaggccagag      360
ctccgccgag tcccgccgcc gtagagggcg tcgccgccgc cgtctccgac taattttgtg      420
ttatgcgatg atgtagagtt actttctatt gtgtgcgtgt aggttttgt tgcatccaat       480 tgtggtaata atactaatcc atcagtttta ttctcattat gtagtgtttg cgtgttgagt      540
gttataaatt gagcttctca ttacattacg tagtgatgtt ggtttctctc tttatgtgca      600
aattgagttt tcttaatatt ttagaattta gataaaaaaa aaaaaaaaaa a               651
```

<210> SEQ ID NO 21
<211> LENGTH: 135
<212> TYPE: PRT
<213> ORGANISM: Glycine max

<400> SEQUENCE: 21

```
Met Ser Asp Thr Glu Thr Thr Pro Glu Gln Pro Ser Thr Pro Pro Gln
 1               5                  10                  15

Thr Glu Ala Pro Pro Gln Pro Asp Pro Ser Ala Ala Val Ser Phe Ser
            20                  25                  30

Ile Trp Pro Pro Thr Gln Arg Thr Arg Asp Ala Val Val Lys Arg Leu
        35                  40                  45

Ile Glu Thr Leu Ser Ala Pro Ser Val Leu Ser Lys Arg Tyr Gly Thr
    50                  55                  60

Leu Ser Ser Asp Glu Ala Ser Ala Ala Arg Gln Ile Glu Asp Glu
65                  70                  75                  80

Ala Phe Cys Ala Ala Thr Ala Ala Ser Ala Ser Ala Ala Ala Asp Gly
                85                  90                  95

Ile Glu Thr Leu Gln Val Tyr Ser Lys Glu Ile Ser Lys Arg Met Leu
            100                 105                 110

Asp Thr Val Lys Ala Arg Ala Pro Pro Ser Pro Ala Ala Val Glu Gly
        115                 120                 125

Val Ala Ala Ala Val Ser Asp
    130                 135
```

<210> SEQ ID NO 22
<211> LENGTH: 485
<212> TYPE: DNA
<213> ORGANISM: Glycine max

<400> SEQUENCE: 22

```
cctcatcgag acccttttccg ccccctccgt cctctccaag cgctacggca ctctctcctc      60
cgacgaatcc tcctccgccg cccgccagat cgaggacgag gccttctccg ctgccgcctc      120
ctccgctgcc tcctcttccg acggcattga gaccctccag gtctactcca aggagatcag      180
caagcgcatg ctcgacaccg ttaaggccag agctgcgccg attccctccg ccgaagaggg      240
cgtcgccgcc tccgtctccg actaattgtg tgttctgcga tgatgtagag ttactttctc      300
ttgtgtgcgt gtaggttttt gttgcatcca attgtggtaa taatattaat ccatcaattt      360
cattctcatc atgtagtgtt tgcgtgttga gttttataaa ttgagcttct cagattttgt      420
gcgcgattga aactatattt atctcaggtt agtaatagtt acatagtaaa aaaaaaaaa       480 aaaaa                                                                  485
```

<210> SEQ ID NO 23
<211> LENGTH: 87
<212> TYPE: PRT

<213> ORGANISM: Glycine max

<400> SEQUENCE: 23

```
Leu Ile Glu Thr Leu Ser Ala Pro Ser Val Leu Ser Lys Arg Tyr Gly
 1               5                  10                  15

Thr Leu Ser Ser Asp Glu Ser Ser Ala Ala Arg Gln Ile Glu Asp
            20                  25                  30

Glu Ala Phe Ser Ala Ala Ala Ser Ser Ala Ser Ser Ser Asp Gly
            35                  40                  45

Ile Glu Thr Leu Gln Val Tyr Ser Lys Glu Ile Ser Lys Arg Met Leu
 50                  55                  60

Asp Thr Val Lys Ala Arg Ala Ala Pro Ile Pro Ser Ala Glu Glu Gly
 65                  70                  75                  80

Val Ala Ala Ser Val Ser Asp
                85
```

<210> SEQ ID NO 24
<211> LENGTH: 557
<212> TYPE: DNA
<213> ORGANISM: Triticum aestivum

<400> SEQUENCE: 24

```
ccgctccctg cctagggttt tgagtcccgc cccctccgc cgcgcaccat gggccccgac      60
gagctcccca aggccgccgc cgccggtgcc gaggaggccg cccgttctc cttcagcatc    120
tggccgccga cgcagcggac gcgggacgcc gtggtgcggc gcctggtgga cacgctggcc    180
ggcgacaccc tcctctgcaa gcgctacggc gccgtgccgg ncgccgacgc cgagcccgcc    240
gcgcgggcca tcgaggtcga ngccttcgac gccgcntcgt caccgnnggg gccgccgcct    300
ccgtcnagga gggcatcgan gngctgcagc tctactccaa ngaggtcagc gccgcctcct    360
cgacttcgtc aagtcncgct ccgccgncgt caangncgan ccgncgggcc gaggangcgn    420
tcnccgtcaa ngaagagacc tcccangctn tacccggac gagaacnttc ggttcgatat    480
gcntccagat aanttatttg atcnnaagtt ccngtgcagt gttggcccttn ttgnataatt    540
ccttngnttt cgntgct                                                    557
```

<210> SEQ ID NO 25
<211> LENGTH: 79
<212> TYPE: PRT
<213> ORGANISM: Triticum aestivum

<400> SEQUENCE: 25

```
Met Gly Pro Asp Glu Leu Pro Lys Ala Ala Ala Gly Ala Glu Glu
 1               5                  10                  15

Ala Ala Pro Phe Ser Phe Ser Ile Trp Pro Pro Thr Gln Arg Thr Arg
            20                  25                  30

Asp Ala Val Val Arg Arg Leu Val Asp Thr Leu Ala Gly Asp Thr Leu
            35                  40                  45

Leu Cys Lys Arg Tyr Gly Ala Val Pro Xaa Ala Asp Ala Glu Pro Ala
 50                  55                  60

Ala Arg Ala Ile Glu Val Xaa Ala Phe Asp Ala Ala Ser Ser Pro
 65                  70                  75
```

<210> SEQ ID NO 26
<211> LENGTH: 584
<212> TYPE: DNA
<213> ORGANISM: Canna edulis -continued

<400> SEQUENCE: 26

```
cccctttttt ctctccttcc gatccgatca gatcaaccgc tcccctcgc cgtccatggc      60
tgaaggcgcc gcctcggaga tgaaggatga agccgaaaag tctgcggtga cggagggagg    120
cgggtacccc tccttgtcct tcaagatctg gcctccgacg cagcggacac gggaggccgt    180
tgtccgccgc ctggtggaga cgctcacctc ccagtctgtc ctatccaagc gctacggagt    240
tatccccgag gaagacgcca catccgccgc ccgcatcatc gaagaggagg cattctccgt    300
cgcctccgtc gcctccgcgg catccaccgg cggccgaccc gaggacgagt ggatagaggt    360
cctccacatc tactcccagg agatcagnca aagagtggtg gagtctgcca aggcgaggac    420
cgaggcagcc tcttcttccg tctctgagag ctatccgggg ggtgggtctc ttcttccgtc    480
tccgagaact atccccgggg gggctctcct ttcactgccg aaatttaggg cggcctcaac    540
tctgccaatg gaggaaacct gggcctcctt tanatgcctg ccgg                     584
```

<210> SEQ ID NO 27
<211> LENGTH: 176
<212> TYPE: PRT
<213> ORGANISM: Canna edulis

<400> SEQUENCE: 27

```
Met Ala Glu Gly Ala Ala Ser Glu Met Lys Asp Glu Ala Glu Lys Ser
 1               5                  10                  15

Ala Val Thr Glu Gly Gly Tyr Pro Ser Leu Ser Phe Lys Ile Trp
            20                  25                  30

Pro Pro Thr Gln Arg Thr Arg Glu Ala Val Val Arg Arg Leu Val Glu
        35                  40                  45

Thr Leu Thr Ser Gln Ser Val Leu Ser Lys Arg Tyr Gly Val Ile Pro
    50                  55                  60

Glu Glu Asp Ala Thr Ser Ala Ala Arg Ile Ile Glu Glu Glu Ala Phe
65                  70                  75                  80

Ser Val Ala Ser Val Ala Ser Ala Ala Ser Thr Gly Gly Arg Pro Glu
                85                  90                  95

Asp Glu Trp Ile Glu Val Leu His Ile Tyr Ser Gln Glu Ile Xaa Gln
            100                 105                 110

Arg Val Val Glu Ser Ala Lys Ala Arg Thr Glu Ala Ala Ser Ser Ser
        115                 120                 125

Val Ser Glu Ser Tyr Pro Gly Gly Gly Ser Leu Leu Pro Ser Pro Arg
    130                 135                 140

Thr Ile Pro Arg Gly Ala Leu Leu Ser Leu Pro Lys Phe Arg Ala Ala
145                 150                 155                 160

Ser Thr Leu Pro Met Glu Glu Thr Trp Ala Ser Phe Xaa Cys Leu Pro
                165                 170                 175
```

<210> SEQ ID NO 28
<211> LENGTH: 483
<212> TYPE: DNA
<213> ORGANISM: Picramnia pentandra

<400> SEQUENCE: 28

```
ccggccttcc actatgtcct ccgaccaaga atcaccgca gaggactcaa ccccacctcc      60
accaccacaa atggaggccc aagcccaagc ccaagatccc cagcccactg aaaagtccca    120
gccgaagaca ccctccagct tcagcttcag catatggccg ccgacacagc gcacccgcga    180
cgccgttttc aaccgactag tggagactct ctcaacccct tcggtccttt cgaagcgtta    240
```

```
cggcaccatt ccctgggat gaggcacctc cgccgctccg tgccatcgaa gaggaggcta      300
tgccgcagcc gggtgcatcc gcctctgccg acgatgacgg catcgagatt ctgcaatcta      360
ttccccgtga gattaagcaa gcgcatgcct tgaaccgtta atgccgattc aatgccaacg      420
caaatgcatc ccggctctgt actganccaa cgaaccaacn agatgtgggg gaaccanccT      480 tcn                                                                    483
```

<210> SEQ ID NO 29
<211> LENGTH: 63
<212> TYPE: PRT
<213> ORGANISM: Picramnia pentandra

<400> SEQUENCE: 29

```
Met Glu Ala Gln Ala Gln Ala Gln Asp Pro Gln Pro Thr Glu Lys Ser
 1               5                   10                  15

Gln Pro Lys Thr Pro Ser Ser Phe Ser Phe Ser Ile Trp Pro Pro Thr
            20                  25                  30

Gln Arg Thr Arg Asp Ala Val Phe Asn Arg Leu Val Glu Thr Leu Ser
        35                  40                  45

Thr Pro Ser Val Leu Ser Lys Arg Tyr Gly Thr Ile Pro Leu Gly
    50                  55                  60
```

<210> SEQ ID NO 30
<211> LENGTH: 1277
<212> TYPE: DNA
<213> ORGANISM: Zea mays

<400> SEQUENCE: 30

```
ccaataccca ccatccccac caacggccgg ccgccgcggc ggagcggagc agagagcaac       60
catggcgtcg aagcagatgg aggagatcca gcggaagcta tccctgctgg agtacccgcg      120
ggcgaacgcc cccgcgcaat ccctcctctt cgccggcgtc gagcgctacc gcctcctcga      180
gtggctcttc ttccggctcc taggcgacag atcgcccttc acgcagcaga actggcaagg      240
ggatagcctg gaccgcgacg aggagaacaa caggatccaa cacctggcgg agatagccaa      300
cttcttgggc atcacacctt cggcggacac cgaggcgatt cagggtcgag gtagctatga      360
ggagcgggtg gaactgctcc atcttattgt tgacctagtg gaagctagtt gctacgctga      420
caatccagaa tggagtgttg ataagcaatt ggagaaggat gtgcaactag tagattcaat      480
tgctgagaaa caagcccaaa ttttttcaga ggagtgcaag cttttccctg cggatgttca      540
aatacaatca atttaccoct tgcctgatat tgctgaacta gagttaaagc tctcggagta      600
taccaaaaag atgtctaatc tgcagcaaat ggttcaggag ttagcatcga agtatgatta      660
taatccaaat gaagactatg cggagacaga gttgaagttg agggaatact tgcaatcatt      720
tttggaaacg gttaaatcct tcaacacaat atatactaag gaaatccatc cttgacccca      780
catgatggaa gtgccacaat tgcatggctt cggtccagct gctaatcgcc tcttggaggc      840
atataatacc cttttaaagt tcttgggaaa tctgaggagc ctccgagatt catacactgc      900
aatggctgct ggttcactgt cggcttctaa tgagccttca tctgtgacca agattatttc      960
agactgcgaa tctgcactca ccttcttgaa tcacagcctt tccatccttt caacttccgt     1020
ggcacgtgag caggggggaa cgctatgatt ttacagtatt tggatagtaa gatatagtca     1080
gtgaacttat gtatgtaagc ttctattaat tcaattgttt gcttcctata aaaaatcagt     1140
tgtttgcatt ttaatttcag ctagtgcatg tactccctttg gatccaaatt ataaattgtt     1200
ttgatatttt ccaaattatg tctagataca caaaaaaaaa aaaaaaaaaa aaaaaaaaa      1260
```

```
aaaaaaaaaa aaaaaa                                               1277

<210> SEQ ID NO 31
<211> LENGTH: 328
<212> TYPE: PRT
<213> ORGANISM: Zea mays

<400> SEQUENCE: 31

Met Ala Ser Lys Gln Met Glu Glu Ile Gln Arg Lys Leu Ser Leu Leu
 1               5                  10                  15

Glu Tyr Pro Arg Ala Asn Ala Pro Ala Gln Ser Leu Leu Phe Ala Gly
             20                  25                  30

Val Glu Arg Tyr Arg Leu Leu Glu Trp Leu Phe Phe Arg Leu Leu Gly
         35                  40                  45

Asp Arg Ser Pro Phe Thr Gln Gln Asn Trp Gln Gly Asp Ser Leu Asp
     50                  55                  60

Arg Asp Glu Glu Asn Asn Arg Ile Gln His Leu Ala Glu Ile Ala Asn
 65                  70                  75                  80

Phe Leu Gly Ile Thr Pro Ser Ala Asp Thr Glu Ala Ile Gln Gly Arg
                 85                  90                  95

Gly Ser Tyr Glu Glu Arg Val Glu Leu Leu His Leu Ile Val Asp Leu
            100                 105                 110

Val Glu Ala Ser Cys Tyr Ala Asp Asn Pro Glu Trp Ser Val Asp Lys
        115                 120                 125

Gln Leu Glu Lys Asp Val Gln Leu Val Asp Ser Ile Ala Glu Lys Gln
    130                 135                 140

Ala Gln Ile Phe Ser Glu Glu Cys Lys Leu Phe Pro Ala Asp Val Gln
145                 150                 155                 160

Ile Gln Ser Ile Tyr Pro Leu Pro Asp Ile Ala Glu Leu Glu Leu Lys
                165                 170                 175

Leu Ser Glu Tyr Thr Lys Lys Met Ser Asn Leu Gln Gln Met Val Gln
            180                 185                 190

Glu Leu Ala Ser Lys Tyr Asp Tyr Asn Pro Asn Glu Asp Tyr Ala Glu
        195                 200                 205

Thr Glu Leu Lys Leu Arg Glu Tyr Leu Gln Ser Phe Leu Glu Thr Val
    210                 215                 220

Lys Ser Phe Asn Thr Ile Tyr Thr Lys Glu Ile His Pro Trp Thr His
225                 230                 235                 240

Met Met Glu Val Pro Gln Leu His Gly Phe Gly Pro Ala Ala Asn Arg
                245                 250                 255

Leu Leu Glu Ala Tyr Asn Thr Leu Leu Lys Phe Leu Gly Asn Leu Arg
            260                 265                 270

Ser Leu Arg Asp Ser Tyr Thr Ala Met Ala Ala Gly Ser Leu Ser Ala
        275                 280                 285

Ser Asn Glu Pro Ser Ser Val Thr Lys Ile Ile Ser Asp Cys Glu Ser
    290                 295                 300

Ala Leu Thr Phe Leu Asn His Ser Leu Ser Ile Ser Thr Ser Val
305                 310                 315                 320

Ala Arg Glu Gln Gly Gly Thr Leu
                325

<210> SEQ ID NO 32
<211> LENGTH: 551
<212> TYPE: DNA
<213> ORGANISM: Triticum aestivum
```

-continued

<400> SEQUENCE: 32

```
ggctcttctt ccggctgctg ggcgacagat cgccgttcac ccagcagaac tggcaggtgg      60
acagcctcga ccgcgacgag gagaacagca ggatccagca cttggcggag atcgcgaatt     120
tcctcggtat cacgccttcg gtcgacactg aggcgattca gggcagaggc agctacgacg     180
agcgggtgga gttcctccgt ctaattgttg acttggtgga agctagctgc tatgccgaca     240
atccagagtg gagtgttgat gagcagttgg caaaggatgt acaacttgta gattccattg     300
ctgagaaaca ggcgcaaatt ttttcggagg agtgcaactt tttcctgcag atgttcaaat     360
acaatcgttt anccctncn tgatatacca ganntagtta anctctctga gtnccaaaaa     420
gntanaantt gcaacagatg gtgcaggagc tncctcaaag tatactatac ncgatgaaga     480
cttnccgaaa agtttaattg gggacnttca atttttctcg aaaagnaatc cttcatntga     540
tnacctaggg a                                                          551
```

<210> SEQ ID NO 33
<211> LENGTH: 126
<212> TYPE: PRT
<213> ORGANISM: Triticum aestivum

<400> SEQUENCE: 33

```
Leu Phe Phe Arg Leu Leu Gly Asp Arg Ser Pro Phe Thr Gln Gln Asn
  1               5                  10                  15

Trp Gln Val Asp Ser Leu Asp Arg Asp Glu Glu Asn Ser Arg Ile Gln
             20                  25                  30

His Leu Ala Glu Ile Ala Asn Phe Leu Gly Ile Thr Pro Ser Val Asp
         35                  40                  45

Thr Glu Ala Ile Gln Gly Arg Gly Ser Tyr Asp Glu Arg Val Glu Phe
     50                  55                  60

Leu Arg Leu Ile Val Asp Leu Val Glu Ala Ser Cys Tyr Ala Asp Asn
 65                  70                  75                  80

Pro Glu Trp Ser Val Asp Glu Gln Leu Ala Lys Asp Val Gln Leu Val
             85                  90                  95

Asp Ser Ile Ala Glu Lys Gln Ala Gln Ile Phe Ser Glu Glu Cys Asn
            100                 105                 110

Phe Phe Leu Gln Met Phe Lys Tyr Asn Arg Leu Xaa Pro Xaa
            115                 120                 125
```

<210> SEQ ID NO 34
<211> LENGTH: 539
<212> TYPE: DNA
<213> ORGANISM: Phaseolus lunatus

<400> SEQUENCE: 34

```
gccattcagg ggcatggaag ctacgaagac cgcactgaaa tgcttcgtct tattgtagat      60
ctagttgagg caacaatatg tgcagataat ccggaatgga gtgttgacga gcaggtagct     120
aaggacatcc aattgattga ttccattgca gaaaacaag ctcaaatatt ttctgaagaa      180
tgcaaattgt ttcctgcaga tgttcagatt cagtccatct atccattgcc agatgtttct     240
gagctggagt caaagttttc tgaacaatca aaaatattgt tgaatcttca acaaaaagtt     300
gatgacttgg catccaagca tgcttaccat ccagatgagg agtataccga ggtggaagcc     360
aactgaggga catttggagc tttctagaac antagaacat tcaatttgat tacaccaagg     420
aattcgtcca tggacacaca tgatggaggt cncacttcat ggattgacag cagccaacgt     480
```

-continued

```
tttgnggcca taaatgcttg aagttttgga acncggatct aggatccatg cacccagct    539
```

<210> SEQ ID NO 35
<211> LENGTH: 121
<212> TYPE: PRT
<213> ORGANISM: Phaseolus lunatus

<400> SEQUENCE: 35

```
Ala Ile Gln Gly His Gly Ser Tyr Glu Asp Arg Thr Glu Met Leu Arg
 1               5                  10                  15

Leu Ile Val Asp Leu Val Glu Ala Thr Ile Cys Ala Asp Asn Pro Glu
            20                  25                  30

Trp Ser Val Asp Glu Gln Val Ala Lys Asp Ile Gln Leu Ile Asp Ser
        35                  40                  45

Ile Ala Glu Lys Gln Ala Gln Ile Phe Ser Glu Glu Cys Lys Leu Phe
    50                  55                  60

Pro Ala Asp Val Gln Ile Gln Ser Ile Tyr Pro Leu Pro Asp Val Ser
65                  70                  75                  80

Glu Leu Glu Ser Lys Phe Ser Glu Gln Ser Lys Ile Leu Leu Asn Leu
                85                  90                  95

Gln Gln Lys Val Asp Asp Leu Ala Ser Lys His Ala Tyr His Pro Asp
            100                 105                 110

Glu Glu Tyr Thr Glu Val Glu Ala Asn
        115                 120
```

<210> SEQ ID NO 36
<211> LENGTH: 412
<212> TYPE: DNA
<213> ORGANISM: Barley sheath

<400> SEQUENCE: 36

```
gaggcatcca cctctgctta tagaagaaga agaagttcct tggaaatttg aggagcctgc    60
gagattcata tacaacaatg gcagctgggt cactttcaaa ttcaagcgag ccttcatcca   120
tcacaaaaat catttcagac tgtgaatccg tgctcacgtt cttaaacaac agccttgcca   180
tcctttcaac ttccgtggca cgggatcagg gtgaaacgct gtgatttat ggccatctta    240 taccaagatt caactctggt aacggatgta actngtagtg atccagtgtt tccttttggt    300
tcagttaggc gcggcttaan gttggtccat tgcggtgtgg ctgtaattgg tgtcttgtga    360
tctttgcagt gnnttgtgcg tcagtgacat gggatctagg agattgcatc tn             412
```

<210> SEQ ID NO 37
<211> LENGTH: 66
<212> TYPE: PRT
<213> ORGANISM: Primer

<400> SEQUENCE: 37

```
Lys Lys Lys Lys Phe Leu Gly Asn Leu Arg Ser Leu Arg Asp Ser Tyr
 1               5                  10                  15

Thr Thr Met Ala Ala Gly Ser Leu Ser Asn Ser Ser Glu Pro Ser Ser
            20                  25                  30

Ile Thr Lys Ile Ile Ser Asp Cys Glu Ser Val Leu Thr Phe Leu Asn
        35                  40                  45

Asn Ser Leu Ala Ile Leu Ser Thr Ser Val Ala Arg Asp Gln Gly Glu
    50                  55                  60

Thr Leu
65
```

```
<210> SEQ ID NO 38
<211> LENGTH: 22
<212> TYPE: DNA
<213> ORGANISM: primer

<400> SEQUENCE: 38
agaattcgga atggcagcag cg                                        22

<210> SEQ ID NO 39
<211> LENGTH: 19
<212> TYPE: DNA
<213> ORGANISM: Primer

<400> SEQUENCE: 39
ggaattctcc aactctagg                                            19
```